US006730792B2

(12) United States Patent
Evers et al.

(10) Patent No.: US 6,730,792 B2
(45) Date of Patent: May 4, 2004

(54) β3 ADRENERGIC AGONISTS

(75) Inventors: Britta Evers, Hamburg (DE); Cynthia Darshini Jesudason, Indianapolis, IN (US); Rushad Eruch Karanjawala, Zionsville, IN (US); David Michael Remick, Fishers, IN (US); Daniel Jon Sall, Greenwood, IN (US); Miles Goodman Siegel, Indianapolis, IN (US); Wolfgang Stenzel, Reinbek (DE); Russell Dean Stucky, Indianapolis, IN (US); John Arnold Werner, Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/311,112

(22) PCT Filed: Jul. 9, 2001

(86) PCT No.: PCT/US01/16519

§ 371 (c)(1),
(2), (4) Date: Dec. 13, 2002

(87) PCT Pub. No.: WO02/06276

PCT Pub. Date: Jan. 24, 2002

(65) Prior Publication Data

US 2003/0191156 A1 Oct. 9, 2003

Related U.S. Application Data

(60) Provisional application No. 60/217,965, filed on Jul. 13, 2000, provisional application No. 60/241,614, filed on Oct. 19, 2000, and provisional application No. 60/292,988, filed on May 23, 2001.

(51) Int. Cl.[7] .................. C07D 401/04; A61K 31/44; C07C 215/20
(52) U.S. Cl. .................. 546/271.1; 546/271.1; 546/280.4; 514/340; 514/342; 564/361; 564/365
(58) Field of Search .................. 546/271.1, 280.4; 514/340, 342; 564/361, 365

(56) References Cited

U.S. PATENT DOCUMENTS 4,276,304 A 6/1981 Ikezaki et al.

FOREIGN PATENT DOCUMENTS

| EP | 0236624 | 9/1987 | | |
|---|---|---|---|---|
| EP | 0611003 | 8/1994 | | |
| EP | 0678511 | 10/1995 | | |
| WO | 9529159 | 11/1995 | | |
| WO | WO-95/29159 | * 11/1995 | ......... | C07D/213/30 |
| WO | 97/10825 | 3/1997 | | |
| WO | 97/46556 | 12/1997 | | |
| WO | 98/09625 | 3/1998 | | |
| WO | 98/32753 | 7/1998 | | |
| WO | 00/40560 | 7/2000 | | |

OTHER PUBLICATIONS

Weber A E, et al; *Bioorganic & Medicinal Chemistry Letters;* 8(16), Aug. 18, 1998; pp. 2111–2116.

Shuker A J, et al; *Tetrahedron Letters;* 38(35, Sep. 1, 1997; pp. 6149–6152.

* cited by examiner

*Primary Examiner*—Alan L. Rotman
*Assistant Examiner*—Janet L Coppins
(74) *Attorney, Agent, or Firm*—Gilbert T. Voy

(57) ABSTRACT

The present invention relates to a $\beta_3$ adrenergic receptor agonist of formula (I) or a pharmaceutical salt thereof, which is capable of increasing lipolysis and energy expenditure in cells and, therefore, is useful for treating Type II diabetes and/or obesity. The compound can also be used to lower triglyceride levels and cholesterol levels or raise high density lipoprotein levels or to decrease gut motility. In addition, the compound can be used to reduced neurogenic inflammation or as an antidepressant agent. Compositions and methods for the use of the compounds in the treatment of diabetes and obesity and for lowering triglyceride levels and cholesterol levels or raising high density lipoprotein levels or for decreasing gut motility are also disclosed.

17 Claims, No Drawings

β3 ADRENERGIC AGONISTS

This application claims the benefit of U.S. Ser. No.'s 60/217,965; 60/241,614; and 60/292,988 filed Jul. 13, 2000, Oct. 19, 2000 and May 23, 2001 respectively.

FIELD OF THE INVENTION

The present invention is in the field of medicine, particularly in the treatment of Type II diabetes and obesity. More specifically, the present invention relates to β$_3$ adrenergic receptor agonists useful in the treatment of Type II diabetes and obesity.

BACKGROUND OF THE INVENTION

The current preferred treatment for Type II, non-insulin dependent diabetes as well as obesity is diet and exercise, with a view toward weight reduction and improved insulin sensitivity. Patient compliance, however, is usually poor. The problem is compounded by the fact that there are currently no approved medications that adequately treat either Type II diabetes or obesity.

One therapeutic opportunity that has recently been recognized involves the relationship between adrenergic receptor stimulation and anti-hyperglycemic effects. Compounds that act as β$_3$ receptor agonists have been shown to exhibit a marked effect on lipolysis, thermogenesis and serum glucose levels in animal models of Type II (non-insulin dependent) diabetes.

The β$_3$ receptor, which is found in several types of human tissue including human fat tissue, has roughly 50% homology to the β$_1$ and β$_2$ receptor subtypes yet is considerably less abundant. Stimulation of the β$_1$ and β$_2$ receptors can cause adverse effects such as tachycardia, arrhythmia, or tremors. An agonist that is selective for the β$_3$ receptor over the β$_1$ and β$_2$ receptors is, therefore, more desirable for treating Type II diabetes or obesity relative to a non-selective agonist.

However, recent studies have suggested the presence of an atypical beta receptor associated with atrial tachycardia in rats (*Br. J. of Pharmacol.*, 118:2085–2098, 1996). In other words, compounds that are not agonists of the β$_1$ and β$_2$ receptors can still modulate tachycardia through activation of a yet to be discovered β$_4$ or through some other unknown pathway.

A large number of publications have appeared in recent years reporting success in discovery of agents that stimulate the β$_3$ receptor. Despite these recent developments, there remains a need to develop a selective β$_3$ receptor agonist which has minimal agonist activity against the β$_1$ and β$_2$ receptors.

SUMMARY OF INVENTION

The present invention relates to a compound of formula I:

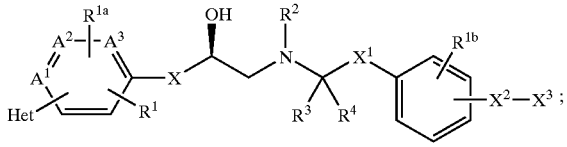

(I)

wherein:
$A^1$, $A^2$ and $A^3$ are carbon or nitrogen provided that only one of $A^1$, $A^2$ and $A^3$ can be nitrogen;

Het is an optionally substituted, optionally benzofused 5 or 6 membered heterocyclic ring;

$R^1$, $R^{1a}$ and $R^{1b}$ are independently H, halo, hydroxy, $C_1$–$C_6$ alkyl, $C_1$–$C_6$ alkoxy, $C_1$–$C_4$ haloalkyl, or $SO_2$ ($C_1$–$C_6$ alkyl);

$R^2$ is H or $C_1$–$C_6$ alkyl;

$R^3$ is H or $C_1$–$C_6$ alkyl;

$R^4$ is H or $C_1$–$C_6$ alkyl;

or $R^3$ and $R^4$ combine with the carbon to which both are attached to form a $C_3$–$C_6$ cyclic ring;

or $R^4$ and $X^1$ combine with the carbon to which both are attached to form a $C_3$–$C_8$ cyclic ring;

or $R^4$ combines with $X^1$, the carbon to which both are attached, and the phenyl group to which $X^1$ is attached to form:

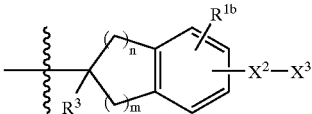

wherein:
n and m are independently 0, 1, 2, or 3 provided that the sum of n+m is ≦4 and that $R^3$ is H;

X is $OCH_2$, $SCH_2$ or a bond;

$X^1$ is a bond or a $C_1$–$C_5$ divalent hydrocarbon moiety;

$X^2$ is O, S, NH, $NHSO_2$, $SO_2NH$, $CH_2$ or a bond; and $X^3$ is optionally substituted phenyl or an optionally substituted 5 or 6 membered heterocyclic ring; or a pharmaceutical salt thereof.

The present invention also relates to processes for preparing, as well as novel pharmaceutical formulations containing, a compound of formula I. In another embodiment, the pharmaceutical formulations of the present invention may be adapted for use in treating Type II diabetes and obesity and for agonizing the β$_3$ receptor.

The present invention also relates to methods for treating Type II diabetes and obesity, as well as a method for agonizing the β$_3$ receptor employing a compound of formula I.

In addition, the present invention relates to a compound of formula I for use in treating Type II diabetes and obesity as well as a compound of formula I for use in agonizing the β$_3$ receptor. The present invention is further related to the use of a compound of formula I for the manufacture of a medicament for treating Type II diabetes and obesity as a well as for agonizing the β$_3$ receptor.

The present invention is also related to a compound of formula II:

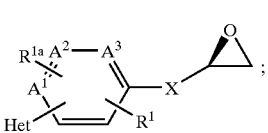

II which is useful as an intermediate to prepare a compound of formula I.

DETAILED DESCRIPTION

For the purposes of the present invention, as disclosed and claimed herein, the following terms are defined below.

The term "halo" represents fluoro, chloro, bromo, or iodo.

The terms "$C_1$–$C_6$ alkyl" and "$C_1$–$C_4$ alkyl" represent a straight, branched or cyclic hydrocarbon moiety having from one to six and one to four carbon atoms, respectively. $C_1$–$C_4$ alkyl groups include methyl, ethyl, n-propyl, isopropyl, cyclopropyl, n-butyl, isobutyl, sec-butyl, t-butyl and cyclobutyl. A "$C_1$–$C_4$ haloalkyl" group is a $C_1$–$C_4$ alkyl moiety substituted with up to six halo atoms, preferably one to three halo atoms. An example of a haloalkyl group is trifluoromethyl. A "$C_1$–$C_6$ alkoxy" group is a $C_1$–$C_6$ alkyl moiety connected through an oxy linkage.

The term "divalent hydrocarbon moiety" refers to a straight or branched chain of carbon atoms that may optionally have one or more points of unsaturation. Thus, a hydrocarbon diradical according to the present invention includes alkylene, alkenylene and alkylidene moieties. Examples include but are not intended to be limited to methylene, ethylene, propylene, butylene, —CH(CH$_3$)CH$_2$——CH(C$_2$H$_5$)CH$_2$—, —CH(CH$_3$)CH(CH$_3$)—, —CH$_2$C(CH$_3$)$_2$—, —CH$_2$CH(CH$_3$)CH$_2$—, —C(CH$_3$)$_2$CH$_2$—, —CH=CHCH$_2$—, —CH=CH—, —C≡CCH$_2$—, and the like.

The term "optionally substituted" as used herein means an optional substitution of one to three, preferably one or two groups independently selected from oxo, nitro, cyano, phenyl, benzyl, halo, $C_1$–$C_6$ alkyl, $C_1$–$C_4$ haloalkyl, COR$^5$, NR$^6$R$^6$, NR$^6$COR$^5$, NR$^6$SO$_2$R$^7$, OR$^6$, OCOR$^5$, OSO$_2$R$^7$, SR$^6$, SOR$^7$, SO$_2$R$^7$ or SO$_2$NR$^6$R$^6$; wherein R$^5$ is H, $C_1$–$C_6$ alkyl, phenyl, benzyl, $C_1$–$C_4$ haloalkyl, NR$^{6a}$R$^{6a}$ or OR$^{6a}$;

R$^6$ and R$^{6a}$ are independently H, $C_1$–$C_6$ alkyl or phenyl; or when two R$^6$ or R$^{6a}$ groups are attached to the same nitrogen atom, said R$^6$ or R$^{6a}$ groups, together with the nitrogen to which they are attached, may combine to form a piperidine, pyrrolidine, hexamethyleneimine or morpholine ring; and R$^7$ is $C_1$–$C_6$ alkyl or phenyl.

The term "heterocyclic ring" represents a stable, saturated, partially unsaturated, fully unsaturated or aromatic ring, said ring having from one to four heteroatoms that are independently selected from the group consisting of sulfur, oxygen, and nitrogen. The heterocycle may be attached at any point which affords a stable structure. Representative heterocyclic rings include 1,3-dioxolane, 4,5-dihydro-1H-imidazole, 4,5-dihydrooxazole, furan, imidazole, imidazolidine, isothiazole, isoxazole, morpholine, oxadiazole, oxazole, oxazolidinedione, oxazolidone, piperazine, piperidine, pyrazine, pyrazole, pyrazoline, pyridazine, pyridine, pyrimidine, pyrrole, pyrrolidine, tetrazole, thiadiazole, thiazole, thiophene and triazole. Representative "benzofused" heterocyclic rings include benzoxazole, benzimidazole, benzofuran, benzothiophene, benzothiazole, azaindole, and indole. Further specific examples of benzofused and non-benzofused heterocycles are described below in the Preparations and Examples sections.

The term "suitable solvent" refers to any solvent, or mixture of solvents, inert to the ongoing reaction that sufficiently solubilizes the reactants to afford a medium within which to effect the desired reaction.

The term "patient" includes human and non-human animals such as companion animals (dogs and cats and the like) and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in aquaculture. Also included are exotic animals used in food production such as alligators, water buffalo and ratites (e.g., emu, rheas or ostriches). The preferred patient of treatment is a human.

The terms "treating" and "treat", as used herein, include their generally accepted meanings, i.e., preventing, prohibiting, restraining, alleviating, ameliorating, slowing, stopping, or reversing the progression or severity of a pathological condition, or sequela thereof, described herein.

The terms "preventing", "prevention of", "prophylaxis", "prophylactic" and "prevent" are used herein interchangeably and refer to reducing the likelihood that the recipient of a compound of formula I will incur or develop any of the pathological conditions, or sequela thereof, described herein.

As used herein, the term "effective amount" means an amount of a compound of formula I that is capable of treating conditions, or detrimental effects thereof, described herein or that is capable of agonizing the $\beta_3$ receptor.

The term "selective $\beta_3$ receptor agonist" means a compound that displays preferential agonism of the $\beta_3$ receptor over agonism of the $\beta_1$ or $\beta_2$ receptor. Thus, $\beta_3$ selective compounds behave as agonists for the $\beta_3$ receptor at lower concentrations than that required for similar agonism at the $\beta_1$ and $\beta_2$ receptors. A $\beta_3$ selective compound also includes compounds that behave as agonists for the $\beta_3$ receptor and as antagonists for the $\beta_1$ and $\beta_2$ receptors.

The term "pharmaceutical" when used herein as an adjective means substantially non-deleterious to the recipient patient.

The term "formulation", as in pharmaceutical formulation, is intended to encompass a product comprising the active ingredient(s) (compound of formula I), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any composition made by admixing a compound of the present invention and a pharmaceutical carrier.

The term "unit dosage form" refers to physically discrete units suitable as unitary dosages for human subjects and other non-human animals, each unit containing a predetermined quantity of active material calculated to produce the desired therapeutic effect, in association with a suitable pharmaceutical carrier.

Because certain compounds of the invention contain an acidic moiety (e.g., carboxy), the compound of formula I may exist as a pharmaceutical base addition salt thereof. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like.

Because certain compounds of the invention contain a basic moiety (e.g., amino), the compound of formula I can also exist as a pharmaceutical acid addition salt. Such salts include the salicylate, sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4 dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate, mandelate and like salts. Preferred acid addition salts include the hemifumarate, benzoate, salicylate, R-mandelate, hydrochloride and glycolate salts.

It is recognized that various stereoisomeric forms of a compound of formula I exist. The compounds may be prepared as racemates and can be conveniently used as such. Therefore, the racemates, individual enantiomers, diastereomers, or mixtures thereof form part of the present invention. Unless otherwise specified, whenever a compound is described or referenced in this specification all the racemates, individual enantiomers, diastereomers, or mixtures thereof are included in said reference or description.

It is also recognized that various tautomeric forms of a compound of formula I may exist, and all tautomeric forms are part of the present invention. Unless otherwise specified, whenever a compound is described or referenced in this specification all tautomeric forms, or mixtures thereof, are included in said reference or description.

PREFERRED COMPOUNDS OF THE INVENTION

Certain compounds of the invention are particularly interesting and are preferred. The following listing sets out several groups of preferred compounds. It will be understood that each of the listings may be combined with other listings to create additional groups of preferred compounds.

a) $A^1$, $A^2$ and $A^3$ are carbon;

b) Het is at the ortho-position relative to X;

c) Het is optionally substituted one to three times independently with halo, hydroxy, oxo, cyano, nitro, phenyl, benzyl, $C_1$–$C_4$ alkyl, $C_1$–$C_4$ haloalkyl, $C_1$–$C_4$ alkoxy, $COR^8$, $CO_2R^8$, $CONR^8R^8$, $NR^8R^8$, NHCO($C_1$–$C_4$ alkyl), NHCO(phenyl), NHCO(benzyl), $SR^8$, SO($C_1$–$C_4$ alkyl), $SO_2$($C_1$–$C_4$ alkyl), $SO_2$($NR^8R^8$), OCO($C_1$–$C_4$ alkyl), $OCO_2R^8$ or $OCONR^8R^8$ where $R^8$ is independently at each occurrence H or $C_1$–$C_4$ alkyl;

d) Het is an optionally substituted 5-membered, non-benzofused ring containing one or two heteroatoms that are independently selected from the group consisting of sulfur, oxygen, and nitrogen;

e) Het is selected from furan; isothiazole; isoxazole; oxazole; and thiophene; wherein said Het moieties are optionally substituted once with fluorine, methyl, cyano, $SO_2NH_2$ or $COCH_3$;

f) Het is selected from thien-2-yl; thien-3-yl; thiazol-2-yl; isoxazol-3-yl; isoxazol-5-yl; and isothiazol-5-yl;

g) Het is thien-2-yl optionally substituted once with fluorine, methyl, cyano, $SO_2NH_2$ or $COCH_3$;

h) Het is thien-2-yl;

i) $R^1$, $R^{1a}$ and $R^{1b}$ are independently H, halo, $C_1$–$C_4$ alkyl, $C_1$–$C_4$ alkoxy, $C_1$–$C_4$ haloalkyl, or $SO_2$($C_1$–$C_4$ alkyl);

j) $R^1$ is H, methyl, ethyl, $CF_3$, chloro or fluoro;

k) $R^1$ is H, methyl, chloro or fluoro;

l) $R^1$ is H or fluoro;

m) $R^1$ is H;

n) $R^{1a}$ is H, methyl, ethyl, $CF_3$, chloro or fluoro;

o) $R^{1a}$ is H, methyl, chloro or fluoro;

p) $R^{1a}$ is H;

q) $R^{1b}$ is H, methyl, ethyl, $CF_3$, chloro or fluoro;

r) $R^{1b}$ is H, methyl, chloro or fluoro;

s) $R^{1b}$ is H;

t) $R^2$ is H or $C_1$–$C_4$ alkyl;

u) $R^2$ is H;

v) $R^3$ and $R^4$ are independently H or $C_1$–$C_4$ alkyl;

w) $R^3$ is H or methyl;

x) $R^4$ is H or methyl;

y) $R^3$ and $R^4$ are both methyl;

z) $R^8$ is independently at each occurrence H or $C_1$–$C_4$ alkyl;

aa) X is $OCH_2$;

bb) $X^1$ is a bond, methylene or ethylene;

cc) $X^1$ is methylene;

dd) $X^2$ is at the para-position relative to $X^1$;

ee) $X^2$ is a bond or O;

ff) $X^2$ is O or $CH_2$;

gg) $X^2$ is O;

hh) $X^3$ is optionally substituted one to three times independently with halo, hydroxy, oxo, cyano, nitro, phenyl, benzyl, $C_1$–$C_4$ alkyl, $C_1$–$C_4$ haloalkyl, $C_1$–$C_4$ alkoxy, $COR^8$, $CO_2R^8$, $CONR^8R^8$, $NR^8R^8$, NHCO($C_1$–$C_4$ alkyl), NHCO(phenyl), NHCO(benzyl), $SR^8$, SO($C_1$–$C_4$ alkyl), $SO_2$($C_1$–$C_4$ alkyl), $SO_2$($NR^8R^8$), OCO($C_1$–$C_4$ alkyl), $OCO_2R^8$ or $OCONR^8R^8$;

ii) $X^3$ is phenyl, pyridyl, thienyl or furanyl wherein said $X^3$ moieties are substituted one to three times with fluoro, chloro, cyano, hydroxy, methyl, ethyl, trifluoromethyl, methoxy, ethoxy, amino, $CO_2CH_3$, $CO_2CH_2CH_3$, $CONR^8R^8$, $SCH_3$, $SCH_2CH_3$, $SOCH_3$, $SOCH_2CH_3$, $SO_2CH_3$ or $SO_2CH_2CH_3$;

jj) $X^3$ is phenyl, pyridyl, thienyl or furanyl wherein said $X^3$ moieties are substituted one to three times with fluoro, cyano, hydroxy, methyl, ethyl, methoxy, ethoxy, amino, $CO_2CH_3$, $CO_2CH_2CH_3$, $CONH_2$, $SCH_3$, $SCH_2CH_3$, $SOCH_3$, $SOCH_2CH_3$, $SO_2CH_3$ or $SO_2CH_2CH_3$;

kk) $X^3$ is phenyl, pyridyl, thienyl or furanyl wherein said $X^3$ moieties are substituted one to three times with fluoro, amino, $CO_2CH_3$, $CO_2CH_2CH_3$, cyano, $CONH_2$, $SO_2CH_3$ or $SO_2CH_2CH_3$;

ll) $X^3$ is phenyl, pyridyl or pyridazinyl wherein said $X^3$ moieties are substituted once or twice with chloro, cyano, $CONH_2$ or $SO_2CH_3$;

mm) $X^3$ is phenyl, pyridyl, thienyl or furanyl wherein said $X^3$ moieties are substituted once with cyano or $CONH_2$;

nn) $X^3$ is phenyl or pyridyl wherein said $X^3$ moieties are substituted once with cyano or $CONH_2$;

oo) $X^3$ is pyridyl substituted once with cyano or $CONH_2$;

pp) $X^3$ is 5-cyano or 5-carboxamido-pyrid-2-yl;
qq) $X^3$ is 4-cyano or 4-carboxamido-phenyl;
rr) $X^3$ is 3-cyano or 3-carboxamido-pyrid-2-yl;
ss) $X^3$ is 2-cyano or 2-carboxamido-phenyl;
tt) the compound of formula I is an acid addition salt;
uu) the compound of formula I is the hydrochloride salt;
vv) the compound of formula I is the glycolate salt;
ww) the compound of formula I is the hemi-fumarate salt.

Synthesis

The compound of formula I may be prepared as described in the following Schemes and Examples.

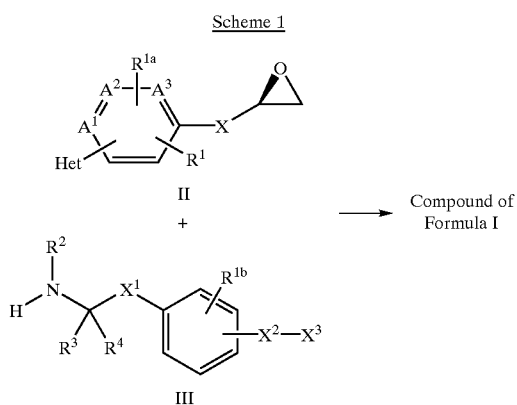

Scheme 1

The reaction of Scheme 1 may be carried out under conditions appreciated in the art for the amination of epoxides. For example, the epoxide of formula II may be combined with an amine of formula III in a lower alcohol, dimethylformamide, dimethylsulfoxide, or acetone, preferably ethanol, isopropanol, n-butanol or t-butanal, at room temperature to the reflux temperature of the reaction mixture, preferably between 40° C.–90° C. The reaction may also be carried out under conditions generally described in Atkins, et al., *Tet. Let.*, 27:2451, 1986. These conditions include mixing the reagents in the presence of trimethylsilyl acetamide in a polar aprotic solvent such as acetonitrile, dimethylformamide, acetone, dimethylsulfoxide, dioxane, diethylene glycol dimethyl ether, tetrahydrofuran, or other polar aprotic solvents in which the reagents are soluble.

The compound of formula I may also be prepared via a Suzuki coupling as shown in Scheme 2.

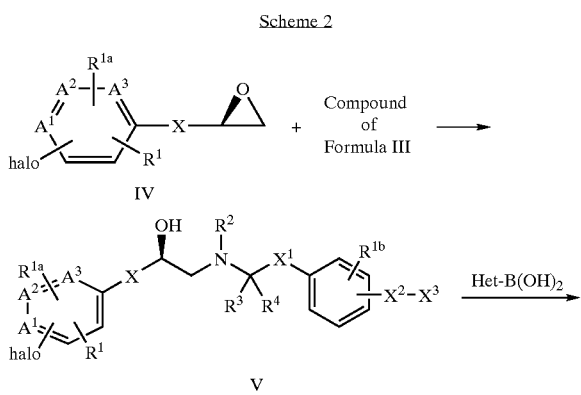

Scheme 2

A compound of formula IV may be reacted with a compound of formula III as described above in Scheme 1. The compound of formula V (an aryl halide) may then be reacted with a heteroaryl boronic acid, an aryl boronic ester, or an aryl boronic cyclic ester, preferably an aryl boronic acid, under conditions appreciated in the art for the coupling of aromatic halides with aryl boronic acids and their derivatives. This coupling is known in the art generally as a Suzuki coupling. The skilled artisan will recognize that an aryl triflate may also be employed in the present Suzuki coupling as an alternative to employing an aryl halide.

The epoxide starting materials employed in Schemes 1 and 2 may be prepared by techniques recognized and appreciated by one skilled in the art. See, e.g., U.S. Pat. No. 4,663,334; European Patent Application 171209; Korn, et al., *J. Pharm. Sci.*, 69(9):1010–13, 1980 and references cited below in the Preparations section for representative and/or analogous procedures for preparing the epoxides of formula II and IV. To illustrate, epoxides of formula II, where X is $OCH_2$ or $SCH_2$, may be prepared according to the procedure detailed in Scheme 3 wherein $R^9$ is OH or SH and X' is $OCH_2$ or $SCH_2$.

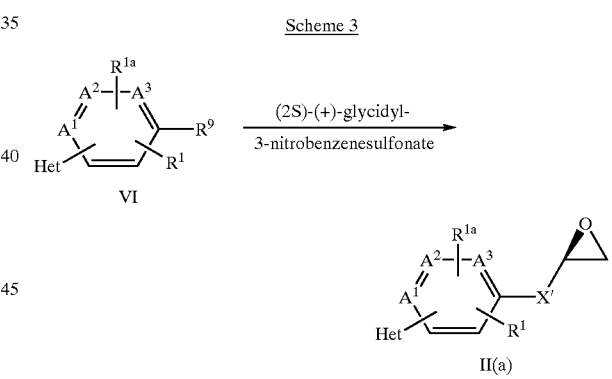

Scheme 3

Equimolar amounts of a compound of formula VI and (2S)-(+)-glycidyl 3-nitrobenzenesulfonate may be dissolved in an inert solvent such as acetone and treated with a slight excess of a weak base, such as potassium carbonate. The suspension may then be heated at reflux for 16–20 hours with stirring to provide a compound of formula II(a). Compounds of formula IV, where X is $OCH_2$ or $SCH_2$, may be prepared in an analogous fashion.

The amino starting materials employed in Schemes 1 and 2 (formula III compound) may also be prepared by techniques recognized and appreciated by one skilled in the art. For example, an amine of formula III, where $X^2$ is O, may be prepared according to the procedure detailed in Scheme 4.

Scheme 4

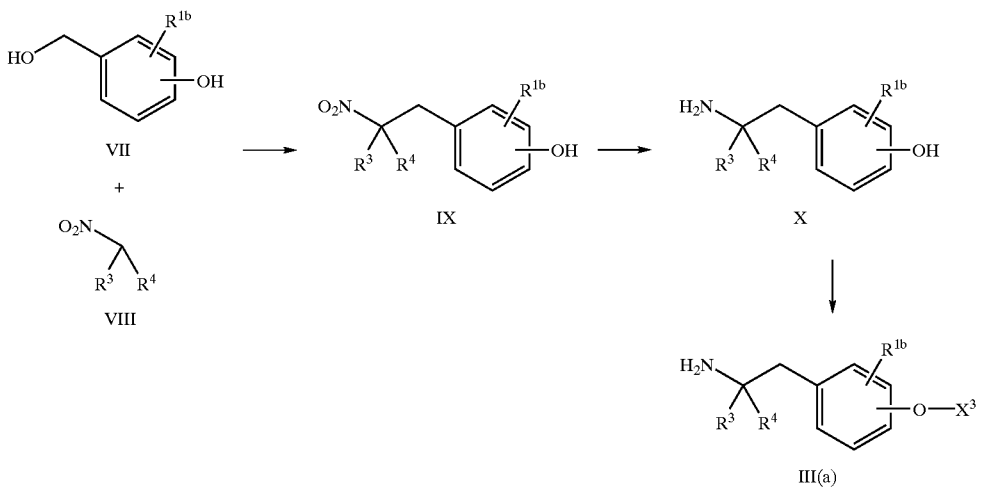

A compound of formula IX may be prepared by reacting an arylalkyl alcohol of formula VII with excess (5 mol/ equivalent) formula VIII compound by methods well known in the art (see, e.g., *Sh. Prikl. Kin.,* 45:1573–77, 1972). The reaction may also be carried out by mixing the reagents in an aprotic solvent, preferably diglyme, and adding potassium t-butoxide (0.5 mol/equivalent). The reaction is typically heated at reflux until water present in the reaction mixture is removed (generally 2–8 hours). A compound of formula X may then be prepared by hydrogenation of the corresponding compound of formula IX over a precious metal catalyst. The hydrogenation can be affected at between 20 and 60 psi of hydrogen (preferably 50 psi), and with a variety of solvents (preferably methanol/acetic acid), temperatures (preferably 50° C.), and catalysts (preferably 5% palladium on carbon wetted with ethanol denatured with toluene) well known in the art.

A skilled artisan will appreciate that a compound of formula X could be coupled with a wide variety of halides to yield the claimed ethers. The coupling can be carried out according to procedures well known in the art and is preferably performed by mixing the starting materials in N,N-dimethylacetamide and toluene in the presence of potassium carbonate. The reaction is typically then heated to reflux for 5 to 24 hours to effect the reaction and to remove water present in the reaction mixture.

Compounds of formula VI, VII and VIII are either commercially available, known in the art, or can be prepared by methods known in the art or described herein.

The following Preparations, Examples and Formulations are provided so that the invention might be more fully understood. They should not be construed as limiting the invention in any way.

Preparations

Epoxides of Formula II and IV

Epoxides 1–21, 23–54 and 56–74 are prepared for use as described in Scheme 1. Epoxides 22 and 55 are prepared for use as described in Scheme 2. These epoxides are pictured in Tables 1 and 2 below.

TABLE 1

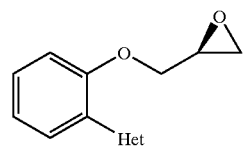

Het =

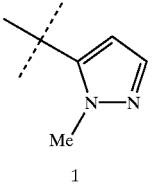

1

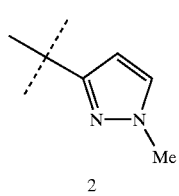

2

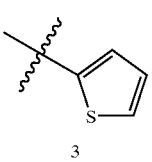

3

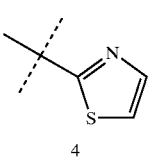

4

TABLE 1-continued
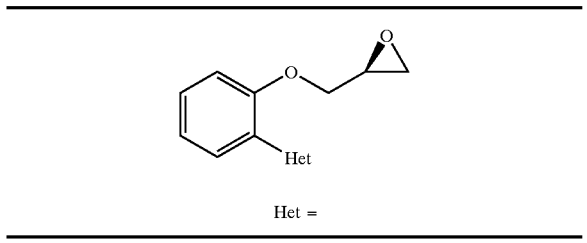
Het =
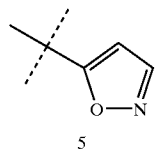
5
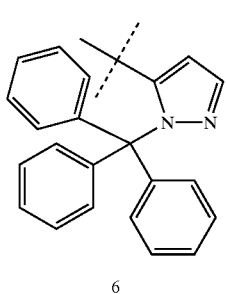
6
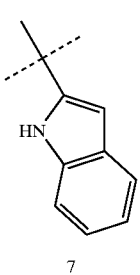
7
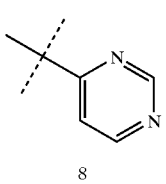
8
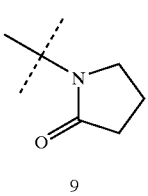
9
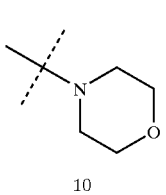
10
TABLE 1-continued
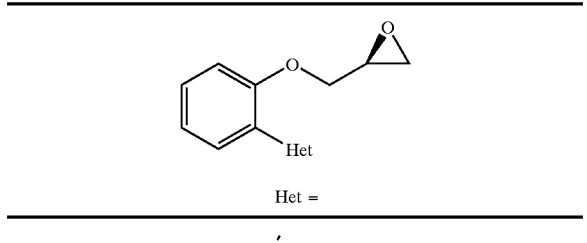
Het =
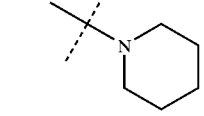
11
12
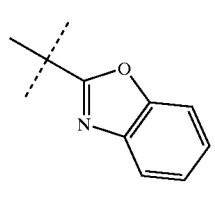
13
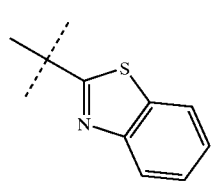
14
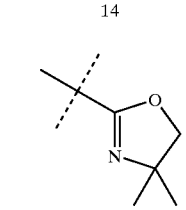
15
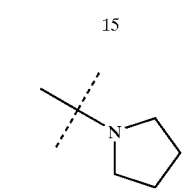
16
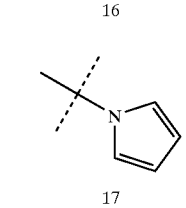
17

TABLE 1-continued
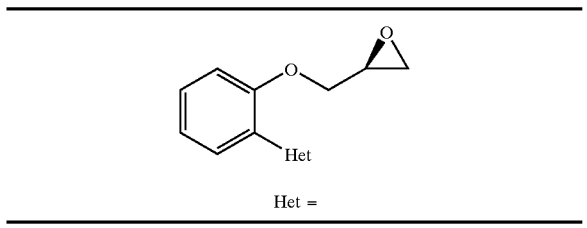
Het =
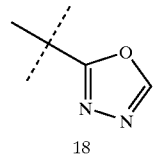
18
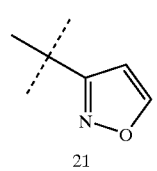
21
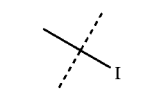
22
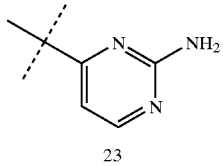
23
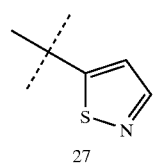
27
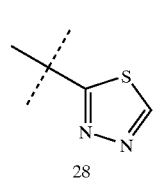
28
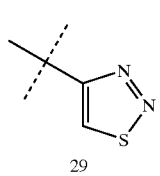
29
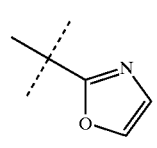
32
TABLE 1-continued
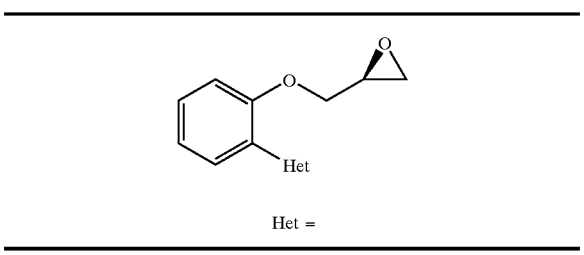
Het =
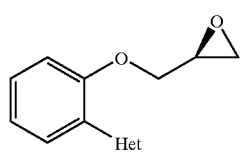
33
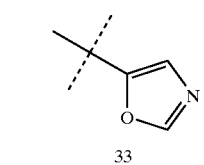
34
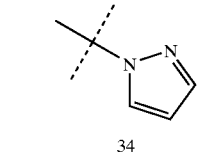
35
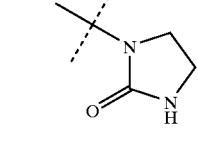
36
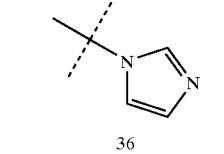
38
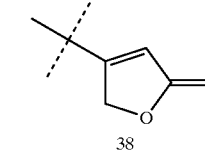
40
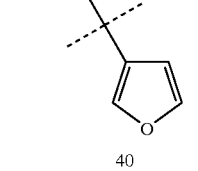
41

TABLE 1-continued
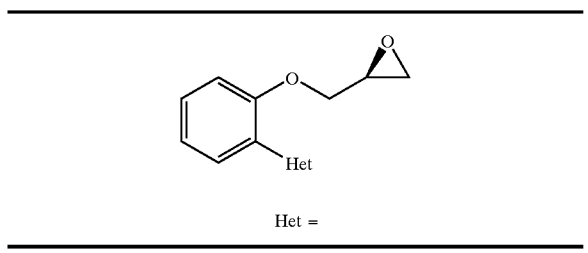
Het =
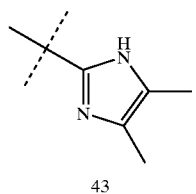
43
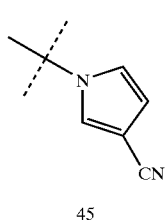
45
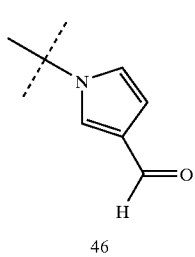
46
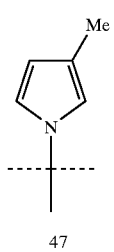
47
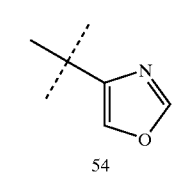
54
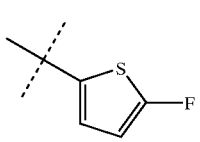
58
TABLE 1-continued
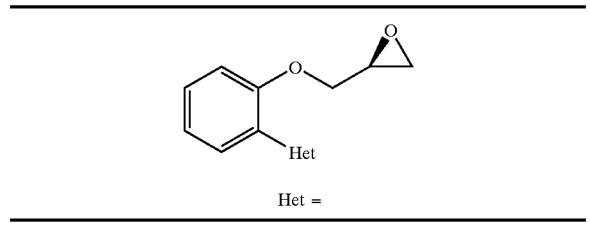
Het =
62
63
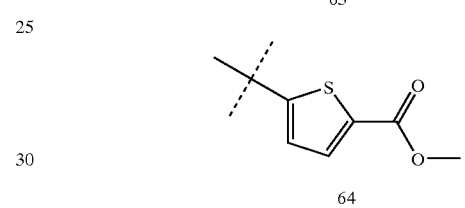
64
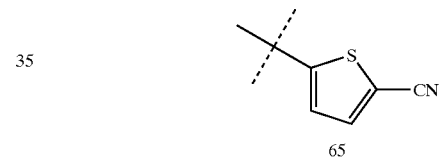
65
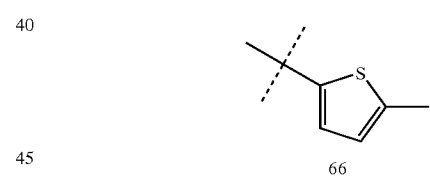
66
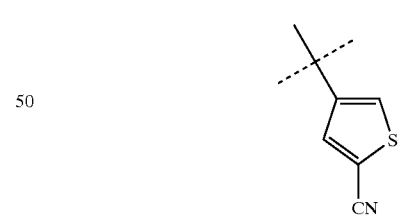
67
68

TABLE 1-continued
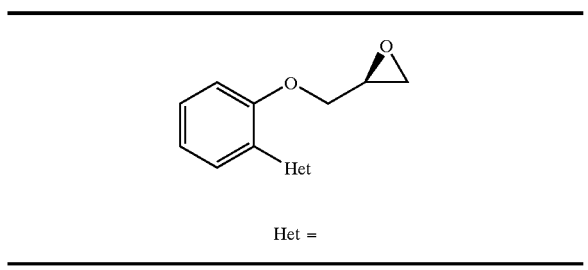
Het =
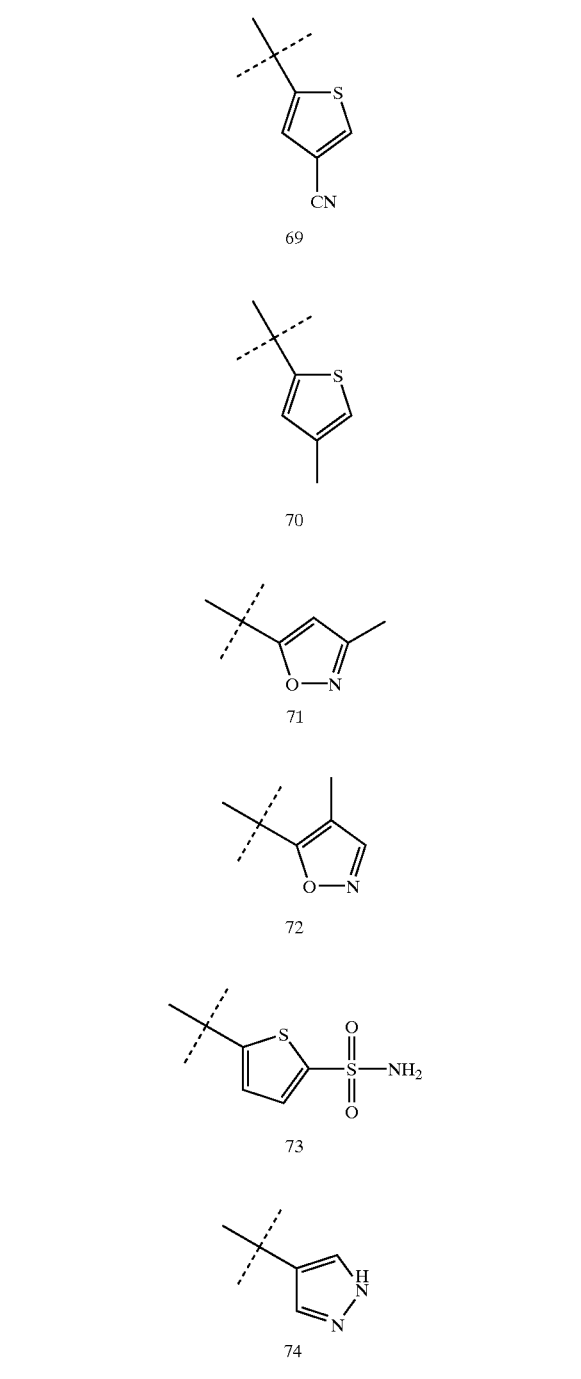
TABLE 2
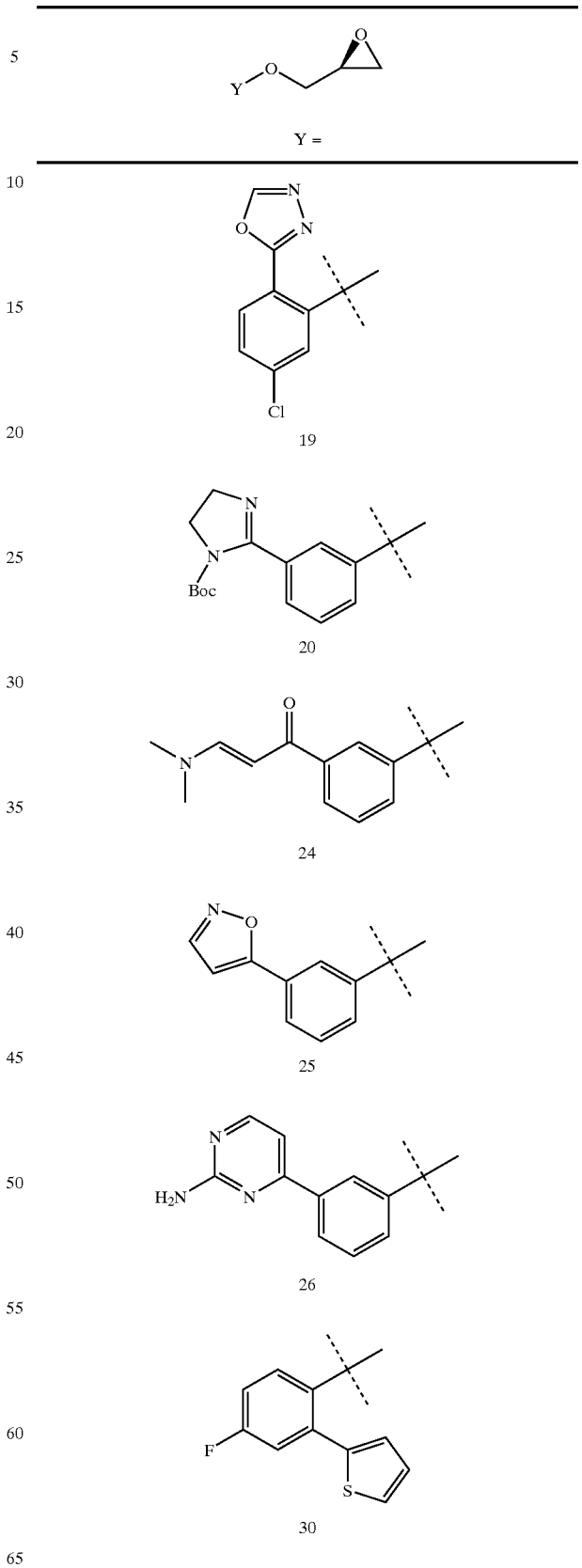

TABLE 2-continued
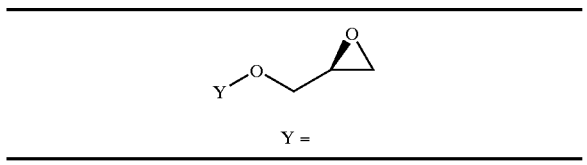
Y =
31
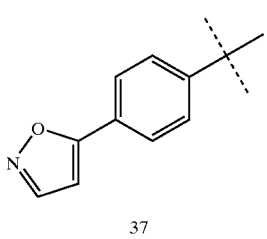
37
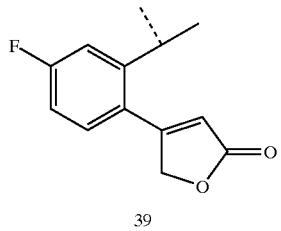
39
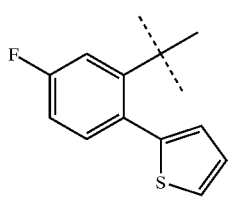
48
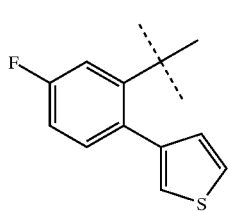
49
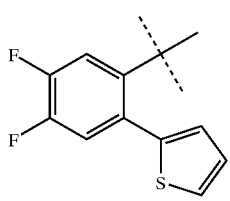
50
TABLE 2-continued
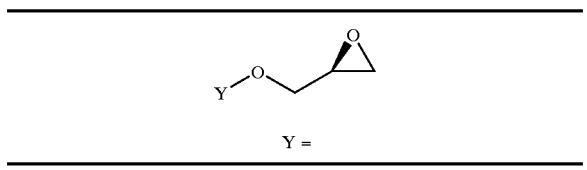
Y =
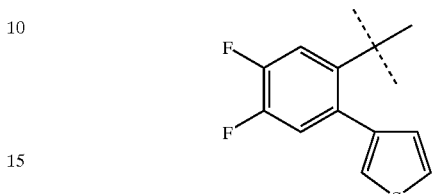
51
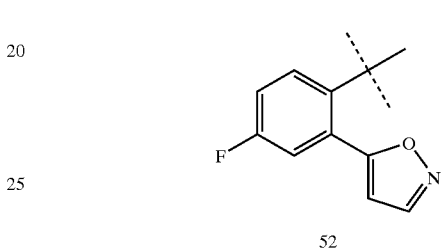
52
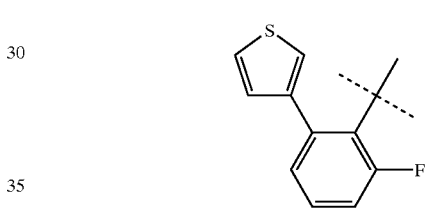
53
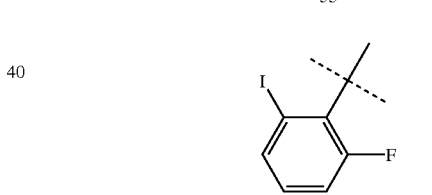
55
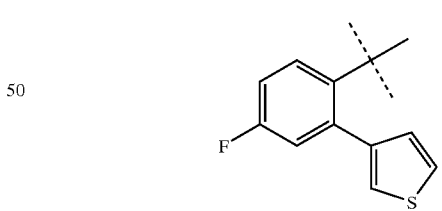
56
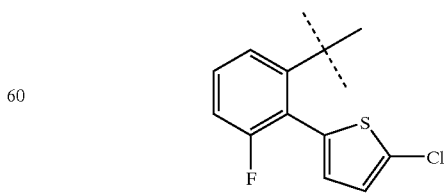
57

TABLE 2-continued

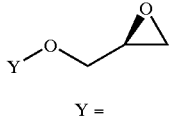

Y =

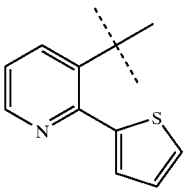

59

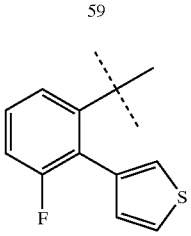

60

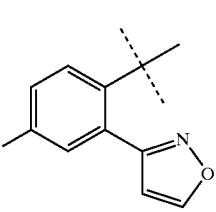

61

Epoxide 1

A mixture of 2-(1-methylpyrazol-5-yl)phenol (4.65 mmol, 810 mg), (2S)-glycidyl 3-nitrobenzenesulfonate (5.58 mmol, 1.45 g), potassium carbonate (5.58 mmol, 771 mg) and acetone (40 ml) are refluxed for 16 hours, cooled to room temperature and the solids removed via filtration. The filtrate is concentrated and the crude product purified on silica gel (40% ethyl acetate/hexane) to give 956 mg of the title epoxide.

Epoxide 2

Methyl hydrazine (23.2 mmol, 1.23 ml) is added to a solution of 2-(3-hydroxy-2-propen-1-on-1yl)phenol (*J. Am. Chem. Soc.*, 72:3396, 1950), 15.4 mmol, 2.54 g) in methanol (7 ml) and the mixture is heated at 100° C. for one hour. After cooling, the reaction mixture is diluted with water (100 ml) and stirred for one hour. The precipitate is collected via filtration and purified on silica gel (30% ethyl acetate/hexane) to give 811 mg of 2-(1-methylpyrazol-3-yl)phenol.

A mixture of 2-(1-methylpyrazol-3-yl)phenol (4.59 mmol, 800 mg), (2S)-glycidyl 3-nitrobenzenesulfonate (5.51 mmol, 1.42 g), potassium t-butoxide (5.51 mmol, 515 mg) and tetrahydrofuran (30 ml) are refluxed for 16 hours, cooled to room temperature and poured into saturated aqueous ammonium chloride. The aqueous layer is extracted with ethyl acetate (3×) and the extracts washed with brine, dried over magnesium sulfate, and concentrated in vacuo. The crude product is purified on silica gel (40% ethyl acetate/hexane) to give 785 mg of the title epoxide.

Epoxide 6

A mixture of 2-(pyrazol-5-yl)phenol (Catalan, et al., *J. Am. Chem. Soc.*, 114(13):5039–48, 1992, 10 mmol, 1.60 g), triethylamine (40.0 mmol, 5.6 ml), and acetonitrile (55 ml) is cooled in an ice bath under $N_2$ and treated dropwise with chlorotrimethylsilane (12.0 mmol, 1.52 ml). After the addition is complete, the cold bath is removed and the reaction mixture stirred at ambient temperature for 1 hour. The reaction mixture is then treated with trityl chloride (10.0 mmol, 2.78 g) and stirred at ambient temperature overnight, followed by refluxing for 1 hour. The reaction mixture is concentrated, treated with saturated aqueous sodium bicarbonate, and extracted with ethyl acetate (3×50 ml). The extracts are dried over magnesium sulfate and concentrated to a viscous oil. The oil is crystallized from 20% ethyl acetate/hexane to give 1.72 g of N-trityl-2-(pyrazol-5-yl) phenol.

A solution of this intermediate phenol (4.27 mmol, 1.72 g) is reacted with (2S)-glycidyl 3-nitrobenzenesulfonate (4.27 mmol, 1.11 g) substantially as decribed for epoxide 2 except that the present reaction is refluxed for 48 hours and the crude product is purified via crystallization from ethyl acetate to give 860 mg of the title epoxide.

Epoxide 7

Phenylhydrazine (476 mmol, 51.5 g) and 2-hydroxyacetophenone (476 mmol, 64.8 g) are stirred under reflux in dry ethanol (280 ml) for 6 hours. After cooling, the crystals are filtered off, washed with cold ethanol and dried under vacuum at 50° C. to yield 73 g (68%) of the hydrazone, which is then mixed with nickel chloride (7 g) and heated under a nitrogen atmosphere to 240° C. for 3 hours. After cooling, the mixture is suspended in dichloromethane (800 ml), salt is removed by filtration and the filtrate is concentrated. The resulting crystals are filtered off, washed with dichloromethane (50 ml) and dried in vacuo at 40° C. to give 16.1 g of 2-(2-indolyl)phenol (24%). This phenolic product is reacted with (2S)-glycidyl 3-nitrobenzenesulfonate substantially as described for Epoxide 1 to yield the title epoxide.

Epoxide 8

2-Hydroxyacetophenone (220 mmol, 30 g) is stirred in a mixture of dimethylformamide-dimethyl acetal for 5 hours at 70° C., cooled and recrystallised from diethylether. The intermediate is dissolved in dry ethanol (200 ml) and formamidine acetate (0.61 mmol, 63.5 g) is added. A solution of sodium (0.61 mol, 14 g) in ethanol (450 ml) is added in several portions and the mixture is refluxed for 18 hours and evaporated. Recrystallisation from diisopropylether yielded 3.6 g (10%) of 2-(pyrimidin-4-yl)phenol as a solid. This phenolic product is reacted with (2S)-glycidyl 3-nitrobenzenesulfonate substantially as described for Epoxide 1 to yield the title epoxide.

Epoxide 19

A mixture of 4-chloro-2-hydroxybenzoic acid hydrazide (Chemical Abstracts, 93:7808, 475 mg, 2.55 mmol) and triethylorthoformate. (3.6 ml) is heated at 130° C. for 3.5 hours. After cooling, a precipitate formed and is collected by filtration. The filter cake is recrystallized from methanol to give 173 mg (35%) of 5-chloro-2-(1,3,4-oxadiazol-2-yl) phenol. This phenolic product is reacted with (2S)-glycidyl 3-nitrobenzenesulfonate substantially as described for Epoxide 1 to yield 170 mg (69%) of the title epoxide.

Epoxide 20

A mixture of methyl 3-hydroxybenzoate (5.48 g, 36.0 mmol) and 1,2-diaminoethane monotosylate (9.85 g, 42.4 mmol) is heated at 210° C. for 7 hours. After cooling, the mixture is stirred with aqueous 2N sodium hydroxide and extracted with ethyl acetate. The precipitate which formed and is present in the aqueous layer is collected by filtration and dried in vacuo to give 1.3 g (22%) of 2-(3-hydroxyphenyl)imidazoline.

To a solution of 2-(3-hydroxyphenyl)imidazoline (0.895 g, 5.52 mmol) in tetrahydrofuran (11 ml) is added water (11 ml), potassium carbonate (1.5 g, 10.8 mmol), then di-t-butyl-dicarbonate (1.2 g, 5.5 mmol). The resulting mixture is stirred over night before additional di-t-butyl-dicarbonate (120 mg) is added and the stirring is continued for several hours. The mixture is diluted with water and extracted with ethyl acetate. The organic layer is washed with brine, dried over sodium sulfate, and concentrated under reduced pressure. The residue is purified via chromatography on silica gel with dichloromethane/ethanol (gradient up to 20:1) to give 615 mg of t-butyl (2-(3-hydroxyphenyl)imidazolin-1-yl)carboxylate (42%). This Boc-protected product (610 mg, 2.33 mmol) is reacted with (2S)-glycidyl 3-nitrobenzenesulfonate substantially as described for Epoxide 1 to yield 720 mg (97%) of the title epoxide.

Epoxide 22

A mixture of 2-iodophenol (5.00 g, 22.7 mmol), (2S)-glycidyl 3-nitrobenzenesulfonate (5.89 g, 22.7 mmol) and potassium carbonate (3.44 g, 24.9 mmol) in methylethylketone (150 ml) is refluxed for 18 hours. After cooling, the salts are removed by filtration. The filter cake is rinsed thoroughly with dichloromethane and the collected filtrates are evaporated. The residue is purified via flash chromatography on silica gel using a hexane-hexane/ethyl acetate gradient (100 to 90:10).

Epoxide 23

Sodium (1.21 g, 52.6 mmol) is added to 200 ml methanol to prepare a solution of sodium methoxide. After addition of guanidine hydrochloride (12.41 g, 129.9 mmol) and 3-(dimethylamino)-1-(2-hydroxyphenyl)-2-propen-1-one (5.0 g, 26.15 mmol; J. Heterocyclic Chem., 14:345, 1977) the mixture is heated at reflux over night. The reaction solvent is removed under reduced pressure, and the residue treated with water. The resulting precipitate is collected by filtration and dried in vacuo to give 4.25 g of 2-amino-4-(2-hydroxyphenyl)pyrimidine (87%). This pyrimidine precursor is reacted with (2S)-glycidyl 3-nitrobenzenesulfonate substantially as described for Epoxide 1 to give 2.05 g of the title epoxide (37.5%).

Epoxide 24

A mixture of 3-hydroxyacetophenone (20.0 g, 146.9 mmol) and N,N-dimethylformamide dimethyl acetal (26.26 g, 220.4 mmol) is heated over night at 100° C. The excess of the acetal is removed under reduced pressure and 3-(dimethylamino)-1-(3-hydroxyphenyl)-2-propen-1-one (10.32 g, 37%) is obtained after chromatography on silica gel with dichloromethane/ethanol 9:1. This intermediate enone is reacted with (2S)-glycidyl 3-nitrobenzenesulfonate substantially as described for Epoxide 1 to give 5.02 g of the title epoxide (78%).

Epoxide 25

A solution of 3-(dimethylamino)-1-(3-hydroxyphenyl)-2-propen-1-one (2.2 g, 11.5 mmol) and hydroxylamine hydrochloride (1.17 g, 16.8 mmol) in 45 ml dioxane/water 1:1 is heated for 2 hours at 60° C. The reaction is poured into ice-water and the precipitate is collected by filtration, washed with water, and dried in vacuo to give 1.4 g of 3-(5-isoxazolyl)phenol (75.5%). This phenolic product is reacted with (2S)-glycidyl 3-nitrobenzenesulfonate substantially as described for Epoxide 1 to give 1.33 g of the title epoxide (70%).

Epoxide 26

2-Amino-4-(3-hydroxyphenyl)pyrimidine, prepared substantially as described for 2-amino-4-(2-hydroxyphenyl)pyrimidine, is reacted with (2S)-glycidyl 3-nitrobenzenesulfonate substantially as described for Epoxide 1 to give the title epoxide.

Epoxide 30

To dioxane (113 ml) is added 2-methoxy-5-fluorophenylboronic acid (4.25 g, 24.9 mmol), 2-bromothiophene (3.65 g, 22.7 mmol, 0.9 eq.) and potassium carbonate (2M, 37 ml). Palladium (0) tetrakistriphenylphoshine (0.03 eq.) is then added and the resulting mixture is heated to 85° C. for 3 hours. The reaction is cooled to room temperature and poured into ethyl acetate and water. The aqueous layer is extracted twice with ethyl acetate. The organic layers are combined, and dried over sodium sulfate, concentrated to a brown oil and the resulting residue is flash chromatographed in 20% toluene/hexanes to afford 11.5 g of 2-(thien-2-yl)-4-fluoroanisole (90%).

The protected product from above (11.0 g, 52.8 mmol) is demethylated with 110 grams of pyridine hydrochloride neat at 200 degrees for 3 hours. The reaction is poured into ice/water and ethyl acetate is added. The layers are separated and the organic layer is washed with water, dried over sodium sulfate and concentrated to a brown solid. This is then flash chromatographed with 1:3 ethyl acetate/hexanes to afford 7.82 g of 2-(thien-2-yl)-4-fluorophenol (77% yield). This phenolic product is reacted with (2S)-glycidyl 3-nitrobenzenesulfonate substantially as described for Epoxide 1 to yield the title epoxide.

Epoxide 31

Epoxide 31 is prepared from 2-methoxy-6-flourophenylboronic acid and 2-bromothiophene by a procedure substantially similar to that described for Epoxide 30.

Epoxide 33

A mixture of 2-methoxybenzaldehyde (10.0 g, 73.4 mmol), tosylmethylisocyanide (14.34 g, 73.4 mmol) and potassium carbonate (10.14 g, 73.4 mmol) in 220 ml methanol is heated at reflux for 6 hours. The solvent is removed under reduced pressure and the residue poured into ice-water (800 ml). The precipitate is collected by filtration, washed with water, and dried in vacuo to give 9.05 g of 5-(2-methoxyphenyl)oxazole (70%).

Boron tribromide (1M in dichloromethane, 36 ml) is added slowly to a cold solution (0° C.) of the above oxazole (3.0 g, 17.1 mmol) in dichloromethane (215 ml). After stirring over night at room temperature, ice-water (50 ml) is added carefully. The aqueous layer is extracted with dichloromethane (50 ml), and the combined organic layers are dried over sodium sulfate and concentrated under reduced pressure. The precipitate which formed after addition of dichloromethane (70 ml) is collected by filtration, heated with dichloromethane (15 ml), and filtered again to give 3.16 g of 2-(5-oxazolyl)phenol. This phenolic product is reacted with (2S)-glycidyl 3-nitrobenzenesulfonate substantially as described for Epoxide 1 to give 400 mg of the title epoxide (9.5%).

Epoxide 34

2-Methoxyphenylboronic acid (2 eq.) and pyrazole (1 eq.) are coupled with copper(II) acetate catalysis as described in Tetrahedron Lett. 39:2941–44, 1998 and the product is demethylated by treatment with boron tribromide in dichloromethane (see, for example, Synth. Commun. 27(20):3581–90, 1997) to yield 2-(pyrazol-1-yl)phenol. This phenolic product is reacted with (2S)-glycidyl 3-nitrobenzenesulfonate substantially as described for Epoxide 1 to give the title epoxide.

Epoxide 35

2-(Imidazolidin-2-on-1-yl)anisole (Ger. Offen. 1977, DE 2528079) is demethylated with boron tribromide and the resulting 2-(imidazolidin-2-on-1-yl)phenol is reacted with (2S)-glycidyl 3-nitrobenzenesulfonate substantially as described for Epoxide 1 to yield the title epoxide.

Epoxide 36

2-(Imidazol-1-yl)anisole (L. M. Sitkina, A. M. Simonov, Khim. Geterotsikl. Soedin 1966, 143) is demethylated with boron tribromide and the resulting 2-(imidazol-1-yl)phenol is reacted with (2S)-glycidyl 3-nitrobenzenesulfonate substantially as described for Epoxide 1 to give the title epoxide.

Epoxide 37

3-(Dimethylamino)-1-(4-hydroxyphenyl)-2-propen-1-one is prepared from 4-hydroxyacetophenone substantially in the same manner as that described for 3-(dimethylamino)-1-(3-hydroxyphenyl)-2-propen-1-one (Epoxide 24). 4-(5-Isoxazolyl)phenol is prepared from 3-(dimethylamino)-1-(4-hydroxyphenyl)-2-propen-1-one substantially in the same manner as that described for 3-(5-isoxazolyl)phenol (Epoxide 25). This phenolic product is reacted with (2S)-glycidyl 3-nitrobenzenesulfonate substantially as described for Epoxide 1 to yield the title epoxide.

Epoxide 45

2-(3-Formyl-1-pyrrolyl)phenol (3 g, 16 mmol) and triethylamine (17.6 mmol) are added to a suspension of hydroxylamine hydrochloride (1.22 g, 17.6 mmol) in acetic anhydride (7.7 ml) and the mixture is allowed to stir overnight at ambient temperature. The mixture is refluxed for 5 hours, concentrated, dissolved in 50 ml ethanol and stirred for 10 min with 50 ml 2 M aqueous sodium hydroxide. After neutralisation with aqueous hydrochloric acid, and extraction with ethylacetate, the organic layer is dried and concentrated. The residue is purified by chromatography (toluene/ethanol 9:1) to yield 2-(3-cyano-1-pyrrolyl)phenol (2.4 g, 92%). This phenolic product is reacted with (2S)-glycidyl 3-nitrobenzenesulfonate substantially as described for Epoxide 1 to yield the title epoxide.

Epoxide 47

To 2-(3-formyl-1-pyrrolyl)phenol (2.9 g, 15.5 mmol) in 50 ml dry tetrahydrofuran are added sodium cyanoborohydride (1.94 g, 31 mmol) and boron trifluoride diethyletherate (5.7 ml, 47 mmol). The resulting solution is stirred for 3 hours at ambient temperature. Saturated sodium bicarbonate (100 ml) is added and the resulting mixture is stirred for 1 hour before extraction with t-butylmethylether. The organic layer is dried and concentrated and the residue is purified by chromatography (toluene/ethanol 9:1) to yield 2-(3-methyl-1-pyrrolyl)phenol (300 mg, 11%). This phenolic product is reacted with (2S)-glycidyl 3-nitrobenzenesulfonate substantially as described for Epoxide 1 to yield the title epoxide.

Epoxide 48

2-Bromo-5-fluoro-phenol (0.87 ml, 7.9 mmol) and 2-thiopheneboronic acid (2.02 g, 15.8 mmol) are dissolved in 100 ml dioxane. The resultingsolution is flushed with argon before tetrakis(triphenylphosphine)palladium (456 mg, 0.395 mmol) and 2 ml of aqueous 2M sodium carbonate solution (20 mmol) are added. After flushing again with argon the mixture is refluxed for 15 hours at 100° C. The solution is allowed to cool to room temperature and the mixture is filtered. The filtrate is evaporated and the residue is taken up in dichloromethane and extracted with water. The organic layer is dried with sodium sulfate then concentrated. The residue is purified by chromatography ($CH_2Cl_2$/EtOH gradient 100:0 to 98:2) to yield 1.13 g of 2-(thien-2-yl)-5-fluorophenol (74%).

2-(Thien-2-yl)-5-fluorophenol and (2S)-glycidyl 3-nitrobenzenesulfonate are reacted as described for the preparation of Epoxide 1 to give the title epoxide.

Epoxides 49–51

2-Bromo-5-fluorophenol is coupled with thiophene-3-boronic acid; 2-bromo-4,5-difluorophenol is coupled with thiophene-2-boronic acid; and 2-bromo-4,5-difluorophenol is coupled with thiophene-3-boronic acid in Suzuki reactions substantially as described for Epoxide 48, to yield 2-(thien-3-yl)-5-fluorophenol; 2-(thien-2-yl)-4,5-difluorophenol; and 2-(thien-3-yl)-4,5-difluorophenol, respectively. These phenolic products are reacted with (2S)-glycidyl 3-nitrobenzenesulfonate substantially as described for Epoxide 1 to yield the title epoxides.

Epoxides 52 and 61

To a solution of 6-fluorochroman-4-one (21.0 g, 126 mmol) in acetic acid (105 ml) is added bromine (6.5 ml, 126 mmol) at such a rate as to not raise the temperature above 25° C. After the addition is complete, the reaction is allowed to stir for 2 hours before pouring into 1 liter of ice. The resulting mixture is stirred over night. The precipitate which formed is filtered and placed in drying oven to produce 21 g of 3-bromo-6-fluorochroman-4-one.

The product from (14 g, 57 mmol) above is dissolved in triethylamine (100 ml) and is stirred at reflux for 2 hours. The reaction is cooled and concentrated, taken up in chloroform, washed with 2N aqueous hydrochloric acid and water. The organic layer is dried over sodium sulfate and concentrated. The product residue is crytallized from hot ethyl acetate.

The product from above (6-fluorochromen-4-one (5.25 g, 32.0 mmol) and hydroxylamine hydrochloride (4.65 g, 67.2 mmol) are dissolved in ethanol (180 ml) and the resulting mixture is heated to reflux. The reaction is allowed to stir for 18 hours before cooling and concentrating. The residue is is taken up in toluene and filtered to give 690 mg of 4-fluoro-2-(isoxazol-5-yl)phenol and from the filtrate 594 mg of 4-fluoro-2-(isoxazol-3-yl)phenol. These phenolic products are separately reacted with (2S)-glycidyl 3-nitrobenzenesulfonate substantially as described for Epoxide 1 to yield the title epoxides.

Epoxide 53

2-Fluoro-6-(thien-3-yl)anisole is prepared from 2-fluoro-6-iodoanisole (1.35 g, 5.36 mmol) by Suzuki coupling with thiophene-3-boronic acid according to the general procedure described in Representative Procedure 4(b) below; yield: 1.05 g (94%).

2-Fluoro-6-(thien-3-yl)phenol is obtained from the anisole (1.0 g, 4.8 mmol) with an excess of boron tribromide in dichloromethane by stirring over night. The crude phenol (1.1 g) is used for the next step without further purification.

Sodium hydride (0.18 g, 4.5 mmol, 60% in oil) is washed several times with hexane under argon and added to a solution of 2-fluoro-6-(thien-3-yl)phenol (0.44 g, 2.26 mmol) and (2S)-glycidyl 3-nitrobenzenesulfonate (0.587 g, 2.26 mmol) in dry tetrahydrofuran (20 ml). After stirring at room temperature over night, the mixture is quenched with ice-cold water, diluted with brine, and extracted with ethyl acetate. The organic layer is dried over sodium sulfate, concentrated under reduced pressure, to give 65 mg (11%) of the title epoxide after chromatography (silica gel, dichloromethane).

Epoxide 54

A mixture of 2-bromo-1-(2-benzyloxyphenyl)ethanone (10.0 g, 32.77 mmol; prepared according to a procedure from *J. Med. Chem.*, 35:3045, 1992) and sodium formate (4.46 g, 65.6 mmol) in dry DMF (100 ml) is stirred at room temperature over night. The mixture is poured into water (400 ml) and extracted with dichloromethane (2×100 ml). The combined extracts are dried over sodium sulfate and concentrated under reduced pressure.

The residue is dissolved in acetic acid (100 ml), treated with ammonium acetate (12.62 g, 163.7 mmol), and the mixture is heated for 3 hours. After cooling, the mixture is diluted with water (400 ml) and extracted with dichloromethane (2×100 ml). The combined organic layers are washed with saturated aqueous sodium bicarbonate solution (2×100 ml), dried over sodium sulfate, and concentrated in vacuo. 4-(2-Benzyloxyphenyl)oxazole (1.99 g, 24%) is obtained after chromatography (silica gel, dichloromethane).

To a solution of the oxazole from above (1.99 g, 7.92 mmol) in dichloromethane (20 ml) is added 10% palladium on carbon (1.99 g). The mixture is put under an atmosphere of hydrogen, stirred at room temperature over night, then filtered through Celite. The solvent is removed under reduced pressure to leave 2-(oxazol-4-yl)phenol (1.15 g, 90%), which is used for the next step without further purification.

The title epoxide (1.05 g, 72%) is prepared from the above phenol (1.08 g, 6.7 mmol) and (2S)-glycidyl 3-nitrobenzenesulfonate substantially as described for Epoxide 1.

Epoxide 55

To a solution of 2-fluoro-6-iodoanisole (Justus Liebigs, Ann. Chem., 746:134, 1971; 4.31 g, 17.1 mmol) in dichloromethane (35 ml) is added a 1M solution of boron tribromide in dichloromethane (18.2 ml). The mixture is kept under argon and stirred for 4 hours at room temperature. The mixture is poured into a saturated aqueous sodium bicarbonate solution and the aqueous layer is extracted with ethyl acetate. The combined organic layers are dried over sodium sulfate and concentrated under reduced pressure to give 2-fluoro-6-iodophenol (4.2 g).

The title epoxide (4.44 g, 86%) is prepared from the above phenol and (2S)-glycidyl 3-nitrobenzenesulfonate substantiallly as described for Epoxide 1 except using butanone as solvent.

Epoxides 56–60

Epoxides 56, 57, 58, 59 and 60 are prepared from 2-methoxy-5-fluorophenylboronic acid and 3-bromothiophene; 2-methoxy-6-fluorophenylboronic acid and 5-chloro-2-bromothiophene; 2-methoxyphenylboronic acid and 2-bromo-5-fluorothiophene; (3-methoxypyrid-2-yl) boronic acid and 2-bromothiophene; and 2-methoxy-6-fluorophenyl and 3-bromothiophene, respectively, by a procedure substantially similar to that described for Epoxide 30.

Epoxide 62

A slurry of 2-cyano phenol (25 g, 209.87 mmol), triethylamine hydrochloride (43.3 g, 314.81 mmol), and sodium azide (20.5 g, 314.81 mmol) in toluene (200 mL) is heated to the reflux temperature of the mixture and then the mixture is allowed to stir at reflux for 15 hours. The mixture is cooled and washed with water (200 mL). The aqueous layer is washed with ether (100 mL), made acidic with concentrated HCl, and the resulting solid is collected by filtration. The solid is washed twice with water (200 mL) and dried under vacuum at 100° C. for 15 hours to give 33.05 g of 2-(tetrazol-3-yl)phenol (97%).

2-(Tetrazol-3-yl)phenol (32.8 g, 202.3 mmol) is dissolved in dimethylformamide (100 mL) and water (25 mL) and cooled in ice. Sodium hydroxide (8.49 g, 212.3 mmol) in water (20 mL) is added and the solution is warmed to ambient temperature. After thirty minutes, iodomethane (31.58 g, 222.5 mmol) is added neat. The solution is stirred for 15 hours then diluted with ethyl acetate (300 mL) and water (500 mL). The aqueous layer is washed three times with ethyl acetate (300 mL) and the organic layers are combined, washed three times with water (1 L), once with brine (1.2 L), dried over magnesium sulfate, filtered and concentrated in vacuo. The solid is purified by flash column chromatography (80% hexane:20% ethyl acetate gradient to 50% hexane:50% ethyl acetate as an eluent) to give 23.5 g of 2-(1-methyltetrazol-3-yl)phenol (66%).

2-(1-Methyltetrazol-3-yl)phenol (0.25 g, 1.54 mmol), (2S)-glycidyl 3-nitrobenzenesulfonate (0.42 g, 1.62 mmol), and potassium carbonate (0.45 g, 3.23 mmol) is dissolved in methyl ethyl ketone (2 mL), the mixture is heated to the reflux temperature of the mixture, and then is allowed to stir at reflux for 15 hours. The slurry is cooled, filtered and concentrated in vacuo. The solid is purified by flash column chromatography (80% hexane:20% ethyl acetate gradient to 50% hexane:50% ethyl acetate as an eluent) to give 270 mg (75%) of the title epoxide. FDMS m/e=233 (M$^+$+1).

Epoxide 63

The title epoxide is prepared from 2-hydroxybenzaldehyde and glyoxal by the method described in *Eur. J. Med. Chem.*, 33:181–187, 1998. This phenolic product is reacted with (2S)-glycidyl 3-nitrobenzenesulfonate substantially as described for Epoxide 1, however, the title epoxide is used without purification as described therein.

Epoxide 64

2-Thienyl-1-methoxybenzene (10 g, 53 mmol) is cooled to −78° C. in dry tetrahydrofuran (265 ml) under nitrogen while stirring. n-Butyl lithium in hexanes (1.6M, 37 ml, 59 mmol, 1.1 eq.) is added slowly and the resulting mixture is stirred cold for an hour. Chloromethyl formate (4.1 ml, 53 mmol, 1.0 equivalent) is added and the reaction is stirred cold for another hour. The mixture is allowed to warm to room temperature before quenching with saturated bicarbonate solution and ethyl acetate. The layers are separated and the organic phase is washed with brine, dried over sodium sulfate and concentrated. The residue is purified via flash chromatography in 5% ethyl acetate/hexanes to afford 7.9 g of 2-(5-methoxycarbonylthien-2-yl)-1-methoxybenzene (61%).

2-(5-Methoxycarbonylthien-2-yl)-1-methoxybenzene is demethylated with boron tribromide to give 1-(5-methoxycarbonylthien-2-yl)phenol. This phenolic product is reacted with (2S)-glycidyl 3-nitrobenzenesulfonate substantially as described for Epoxide 1 to yield the title epoxide.

Epoxide 65

A solution of 5-bromothiophene-2-carbonitrile (1.25 g, 6.65 mmol) in 50 ml of dioxane is degassed with argon, tetrakis-(triphenylphosphine)-palladium(0) (768 mg, 0.665 mmol) is added and the mixture is stirred for 5 minutes. 2-Methoxybenzene boronic acid (2.02 g, 13.3 mmol) and aqueous 2 N sodium carbonate (13.3 ml) are successively added and the mixture is stirred for 16 hours at 85° C. Extractive work-up (2×50 ml dichloromethane and 2×30 ml water). The organic phase is dried over sodium sulfate, filtrated and evaporated. The residue (4.05 g) is purified via flash column on silica (eluent: 100% hexane>hexane/ethyl acetate 96:4 gradient to give 1.37 g of 2-(5-cyanothien-2-yl)anisole (96%). M+=215.

An intimate mixture of 2-(5-cyanothien-2-yl)anisole (1.2 g, 5.9 mmol) and pyridinium hydrochloride (13.7 g, 119 mmol) is heated for 1 hour to 210° C. under argon. The mixture was cooled to ambient temperature and a 1:1 mixture of water and ethyl acetate is added to break and dissolve the solid cake formed during the reaction. The slurry is then transferred to a separation funnel and dichloromethane is added until the organic phase had a higher density than the water phase (organic phase=lower phase). The organic phase contains the desired product and is separated. The remaining aqueous phase is additionally extracted twice with dichloromethane and the collected organic phases are dried over sodium sulfate and evaporated. The residue is purified via flash column on silica (eluent: 100% hexane>hexane/ethyl acetate 8:2 gradient) to give 973 mg of 2-(5-cyanothien-2-yl)phenol (87%). M+=201.

To a solution of 2-(5-cyanothien-2-yl)phenol (970 mg, 4.819 mmol) in 20 ml of dry 2-butanone is added (2S)-glycidyl 3-nitrobenzenesulfonate (1.25 g, 4.82 mmol) and potassium carbonate (732 mg, 5.30 mmol) successively. After stirring for 48 hours at 75° C., the mixture is diluted with ethyl acetate and extracted with 2N aqueous sodium hydroxide (2×30 ml) and water (1×30 ml). (M+=257).

Epoxides 66–70

Epoxides 66–70 are prepared by a procedure substantially similar to that described for Epoxide 65. The starting halogeno thiophenes used to prepare Epoxides 65–70 are known from the literature, see e.g., *J. Mater. Chem.*, 5(4), 653–61, 1995; *J. Chem. Soc.*, Perkin Trans. 2, 5:625–30, 1982; *Chem. Scr.*, 5(5), 217–26, 1974; *Bull. Soc. Chim. Fr.*, 11:4115–20, 1967; *Bull. Soc. Chim. Fr.*, 11:4121–6, 1967; *Bull. Inst. Chem. Res.*, 52(3):561–5, 1974; *J. Med. Chem.*, 43(16):3168–3185, 2000; *Bioorg. Med. Chem. Lett.*, 10(5):415–418, 2000; and JP 08311060.

Epoxide 73

A 25 ml 1-propanol solution of 2-methoxyphenyl boronic acid (1.2 g, 7.5 mmol) and 5-bromothien-2-ylsulfonamide (1.2 g, 5 mmol) is stirred under $N_2$ at room temperature. Palladium(II) acetate (56 mg, 0.25 mmol), triphenylphosphine (200 mg, 0.75 mmol), 2M aqueous $Na_2CO_3$ (3 ml, 6 mmol), and 7 ml $H_2O$ are added and the resulting mixture is refluxed (~88° C.) for 1 hour. The reaction is cooled, diluted with ethyl acetate, washed with brine, and the brine back extracted with ethyl acetate. The extracts are combined, washed with aqueous $NaHCO_3$, brine, dried ($Na_2SO_4$), filtered, and the filtrate is concentrated. The residue is purified by chromatography ($SiO_2$, ethyl acetate/hexane gradient) to give 943 mg (70%) of 5-(2-methoxyphenyl)thiophene-2-sulfonamide.

A 70 ml $CH_2Cl_2$ suspension of 5-(2-methoxyphenyl)thiophene-2-sulfonamide (1.0 g, 3.7 mmol) is stirred under $N_2$ at −75° C. as boron tribromide (1.1 ml, 12 mmol) is syringed into the reaction mixture. The amber solution is stirred for 30 minutes at −75° C., then at 0° C. for 2–3 hours. The reaction is quenched with ice, extracted with $CH_2Cl_2$. The extracts are washed with brine, dried ($Na_2SO_4$), filtered, and the filtrate is concentrated. The residue is purified by chromatography ($SiO_2$, ethyl acetate/hexane gradient) to give 720 mg of 5-(2-hydroxyphenyl)thiophene-2-sulfonamide (76%).

5-(2-Hydroxyphenyl)thiophene-2-sulfonic acid amide (1.8 g, 7.1 mmol), $K_2CO_3$ (1.1 g, 8.5 mmol), and (2S)-glycidyl 3-nitrobenzenesulfonate (2.1 g, 7.8 mmol) are reacted as described for the preparation of Epoxide 1 to give 1.5 g of the title epoxide (70%).

Epoxide 74

(2-Methoxyphenyl)acetaldehyde is prepared by oxidation of 2-(2-methoxyphenyl)ethanol according to the procedure disclosed in *J. Org. Chem.*, 49:1720, 1999. A mixture of (2-methoxyphenyl)acetaldehyde (3.8 g, 25.3 mmol) and dimethylformamide dimethyl acetal (4.52 g, 37.9 mmol) is stirred at room temperature for 1 hour. Excess of the acetal is removed under reduced pressure to leave 4.68 g of 3-dimethylamino-2-(2-methoxyphenyl)propenal (90%).

A solution of 3-dimethylamino-2-(2-methoxyphenyl) propenal (4.68 g, 22.8 mmol) and hydrazine hydrate (6.7 ml) in ethanol (100 ml) is heated at reflux for 30 minutes. The solvent is removed in vacuo and the residue is chromatographed (silica gel, dichloromethane/ethanol 95:5) to give 2.69 g of 4-(2-methoxyphenyl)pyrazole (68%).

To a solution of 4-(2-methoxyphenyl)pyrazole (300 mg, 1.72 mmol) in dichloromethane (13 ml) is added a 1M solution of boron tribromide (3.8 ml) in dichloromethane. The mixture is stirred at room temperature over night then concentrated under reduced pressure. The residue is chromatographed (silica gel, dichloromethane/ethanol 9:1) to give 270 mg of 2-(pyrazol-4-yl)phenol (98%).

2-(Pyrazol-4-yl)phenol and (2S)-glycidyl 3-nitrobenzenesulfonate are reacted as described for the preparation of Epoxide 1 to give 180 mg of the title epoxide (50%).

Epoxides 3–5, 9–18, 21, 27–29, 32, 38–41, 43, 46, 71 and 72

2-(Thien-2-yl)phenol (*J. Heterocycl. Chem.*, 22(6):1667–9, 1985); 2-(thiazol-2-yl)phenol (Arnold, et al., WO 94/22846); 2-(5-isoxazolyl)phenol; 2-(pyrrolidin-2-on-1-yl)phenol (Tetrahedron, 26(17):4207–4212, 1970);

2-morpholinophenol; 2-piperidinophenol; 1-(2-hydroxyphenyl)piperazine; 2-(2-hydroxyphenyl)benzoxazole; 2-(2-hydroxyphenyl)benzothiazole; 2-(4,4-dimethyl-2-oxazolin-2-yl)phenol (*Bioorg. Med. Chem. Lett.,* 6(18):2173–76, 1996); 2-(1-pyrrolidino)phenol; 2-(pyrrol-1-yl)phenol (*J. Het. Chem.,* 8:283–287, 1971); 2-(1,3,4-oxadiazol-2-yl)phenol (WO 94/22846); 2-(isoxazol-3-yl)phenol (*J. Het. Chem.,* 8:283–287, 1971); 2-(isothiazol-5-yl)phenol (*J. Chem. Res.* (S), 349, 1988; *J. Chem. Res.* (S), 163, 1992); 2-(1,3,4-thiadiazol-2-yl)phenol (WO 94/22846); 2-(1,2,3-thiadiazol-4-yl)phenol; 2-(oxazol-2-yl)phenol (WO 94/22846); 4-(2-hydroxyphenyl)-2(5H)-furanone (Ger. Offen. DE2829414); 4-(4-fluoro-2-hydroxyphenyl)-2(5H)-furanone (Ger. Offen. DE2829414); 2-(furan-3-yl)phenol (Ger. Offen. DE2914166); 2-thiazol-4-yl-phenol (WO 94/22846); 2-(thiazol-4-yl)phenol (WO 94/22846); 2-(4,5-dimethylimidazol-2-yl)phenol (*Eur. J. Med. Chem.,* 33:181–187, 1998, using 4,5-dimethylimidazole instead of imidazole); 2-(3-formylpyrrol-1-yl)phenol (*J. Het. Chem.,* 283–287, 1971 using 2,5-dimethoxy-3-formyl-tetrahydrofuran instead of 2,5-dimethoxy-tetrahydrofuran); 2-(3-methylisoxazol-5-yl)phenol (*J. Org. Chem.,* 49:4419, 1984); and 2-(4-methylisoxazol-5-yl)phenol (*Pol. J. Chem.,* 56:501, 1982) are reacted with (2S)-glycidyl 3-nitrobenzenesulfonate substantially as described for Epoxide 1 to yield the title epoxides.

Amines of Formula III

Amines 1–49 are prepared for use as described in Schemes 1 and 2. These amines are pictured in Tables 3–5 below.

TABLE 3

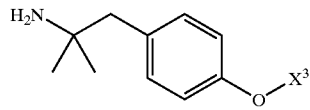

$X^3$ =

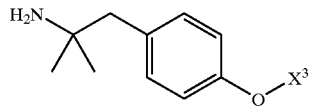

1

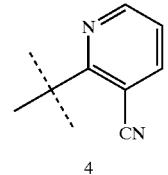

2

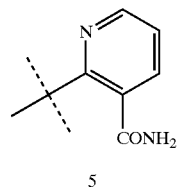

3

TABLE 3-continued

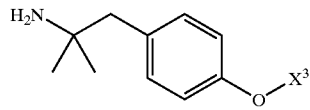

$X^3$ =

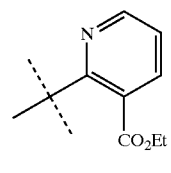

4

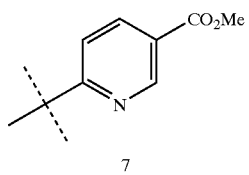

5

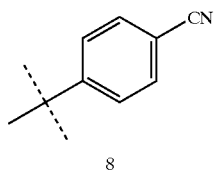

6

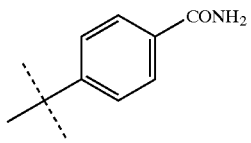

7

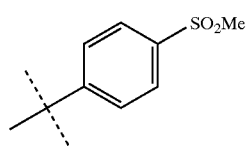

8

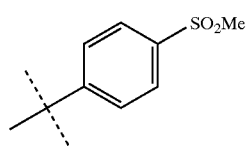

9

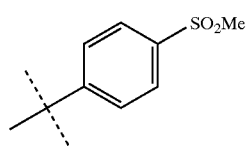

10

TABLE 3-continued
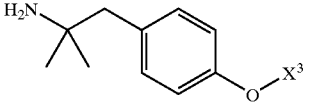
X³ =
| | |
|---|---|
| 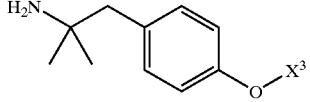<br>11 | 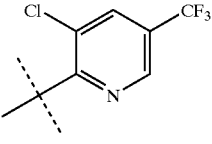<br>18 |
| 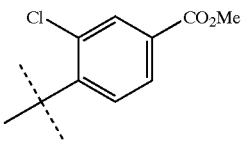<br>12 | 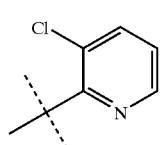<br>19 |
| 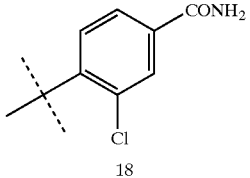<br>13 | 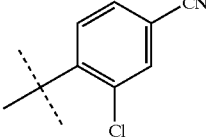<br>20 |
| 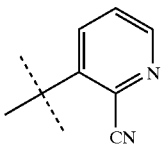<br>14 | 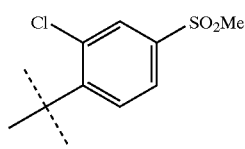<br>21 |
| 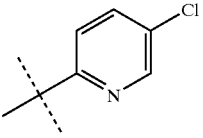<br>15 | 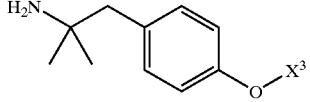<br>22 |
| 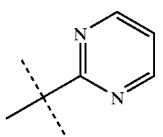<br>16 | 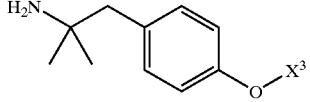<br>23 |
| 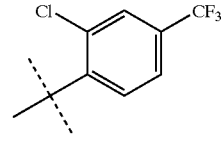<br>17 | 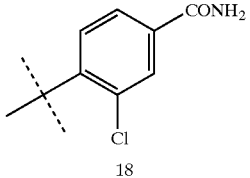<br>24 |

TABLE 3-continued
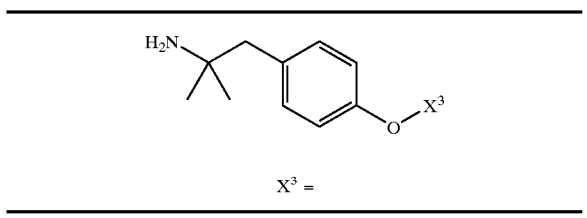
X³ =
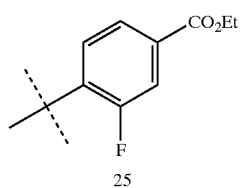
25
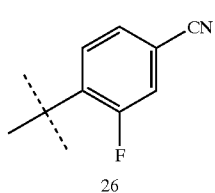
26
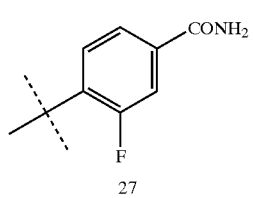
27
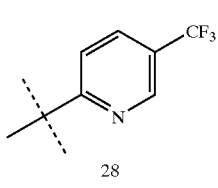
28
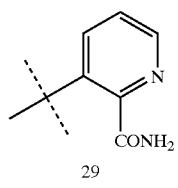
29
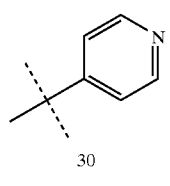
30
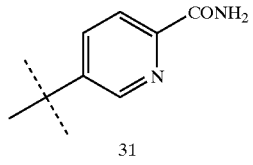
31
TABLE 3-continued
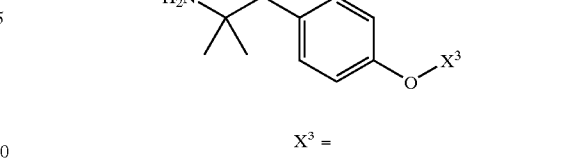
X³ =
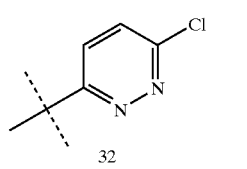
32
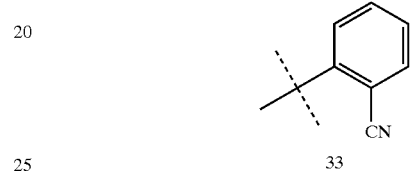
33
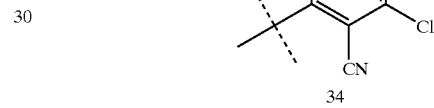
34
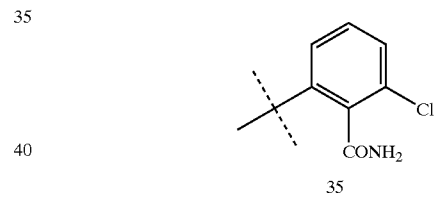
35
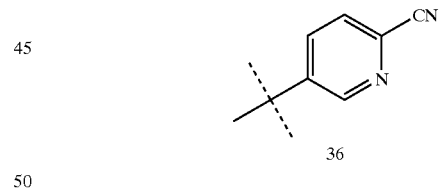
36
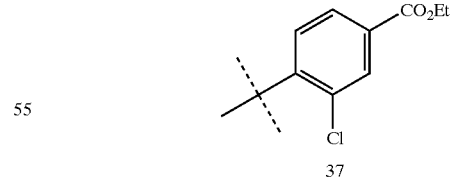
37
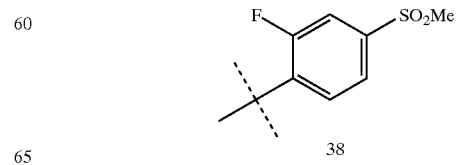
38

TABLE 3-continued

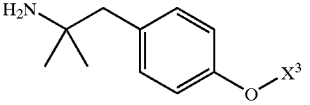

X³ =

| | |
|---|---|
| 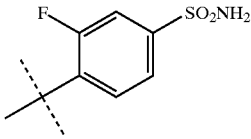 39 | 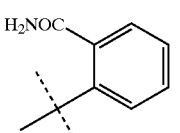 40 |
| 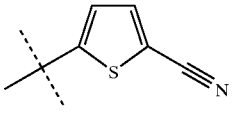 43 | 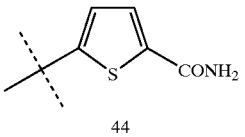 44 |
| 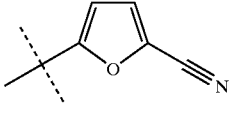 45 | 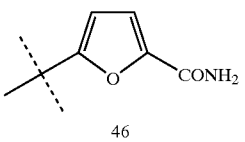 46 |

TABLE 4

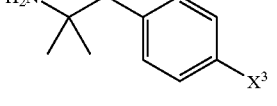

X³ =

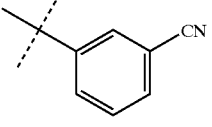
41

TABLE 4-continued

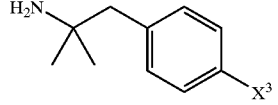

X³ =

| | |
|---|---|
| 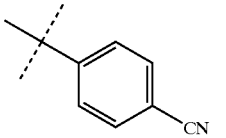 42 | 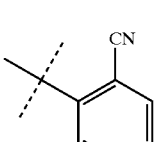 47 |

TABLE 5

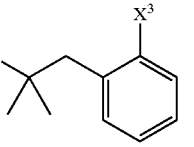

X³ =

| | |
|---|---|
| 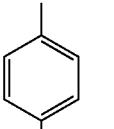 48 | 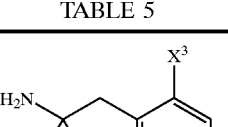 49 |

Amines 1 and 10 may be prepared according to procedures detailed in U.S. Ser. No. 09/068,192, the teachings of which are herein incorporated by reference. Amines 11, 26 and 33 may be prepared by a procedure substantially similar to that described for Amine 1. Amines 2, 3, 8, and 9 may be prepared according to procedures detailed in U.S. Pat. No. 5,977,154, the teachings of which are herein incorporated by reference. Amines 27, 29 and 40 may be prepared by a procedure substantially similar to that described for Amine 9.

Amine 4

4-(2-Amino-2-methylpropyl)phenol (50.8 g, 225 mmol), 2-chloro-3-cyanopyridine (30.8 g, 222 mmol), potassium carbonate (77.7 g, 562 mmol, powdered), N,N-dimethylacetamide (609 ml), and isooctane (122 ml) are combined and heated to reflux. The water formed during the reaction is removed azeotropically via a Dean-Stark trap. After about 1–2 hours the reaction is complete. The slurry is cooled to 30° C. and filtered. The filter cake is washed with N,N-dimethylacetamide (250 ml) and the combined organic fractions are concentrated by rotary evaporation at 80° C. The resulting dark green oil is dissolved in dichloromethane (580 ml), and washed with water (160 ml). The phases are separated and the organic phase washed with water (250 ml). Water (1 L) is added to the organic phase and the pH adjusted to 1 with 12N aqueous hydrochloric acid (about 25 ml). The phases are separated and the acidic aqueous layer is washed with dichloromethane (250 ml). Dichloromethane (1 L) is added to the acidic aqueous phase and the pH is adjusted to 12–13 with 5N aqueous sodium hydroxide. The phases are separated and the organic phase is dried over sodium sulfate. After filtration the solution is concentrated to give 53 g of the title amine (88%).

Amine 6

4-(2-Amino-2-methylpropyl)phenol (55.18 g, 244.9 mmol) is added to 5.05N KOH (97.2 mmol). The mixture is warmed to 50° C. to give a homogeneous yellow solution. Chlorobenzene (1104 ml) and N,N-dimethylacetamide (10.7 g, 122 mmol) is added and the mixture is heated to reflux (about 100° C.). The water is removed azeotropically via a Dean-Stark trap. At about 125° C. a solid began to form. When the pot temperature reached 132° C. the water has been removed and the reaction mixture is a thick but stirable slurry (mechanical stirring required). The Dean-Stark trap is removed and an additional 100 ml of chlorobenzene is removed and discarded. Dry chlorobenzene (50 ml) is added to the slurry, followed by ethyl 2-chloronicotinate (50.0 g, 269 mmol) in chlorobenzene (50 ml). The slurry is heated at reflux until the reaction is complete (about 24 hours). After cooling to room temperature, water (385 ml) and 1N NaOH (25 ml, 0.1 equiv) is added to the mixture and the phases are separated. The organic phase is washed with water (285 ml) and the solution is concentrated to a net weight of 700 g (89%).

Amine 7

4-(2-Amino-2-methylpropyl)phenol (3.00 g, 18.2 mmol), methyl 6-chloronicotinate (3.27 g, 19.1 mmol), powdered potasssium carbonate (3.76 g, 27.2 mmol, 300 mesh), N,N-dimethylacetamide (60 ml), and toluene (15 ml) are combined and heated to reflux. The water formed during the reaction is removed azeotropically via a Dean-Stark trap. After about 2 hours, the internal temperature reached 154° C. and the reaction is complete. The slurry is cooled to 30° C. and filtered. The filter cake is washed with N,N-dimethylacetamide and the combined organic fractions concentrated by rotary evaporation at 75° C. The resulting oil is dissolved in ethyl acetate (50 ml), and washed with water (30 ml). The phases are separated and the aqueous phase is extracted with ethyl acetate (20 ml) after some saturated aqueous sodium chloride solution (10 ml) is added to facilitate phase separation. The combined organic fractions are washed with water (2×30 ml) and saturated aqueous sodium chloride (30 ml) and then dried over sodium sulfate. After filtration the solution is concentrated to give 4.60 g (80%) of the title amine.

Amine 12

2-Cyano-3-chloropyridine (Bremner, et al., *Syn. Comm.*, 27:1535, 1997; Kaneda, et al., *Chem. Pharm. Bull.*, 33:565, 1985) is coupled to 4-(2-amino-2-methylpropyl)phenol to prepare the title amine by a procedure substantially similar to that described above for Amine 4.

Amine 24

Potassium tert-butoxide (58.6 ml, 58.6 mmol, 1M in tetrahydrofuran) is added to a solution of 3,4-dichlorothiophenol (10.0 g, 55.8 mmol) in tetrahydrofuran (300 ml) at 0° C. and the solution stirred for 30 minutes. Methyl iodide (8.32 g, 58.6 mmol) is added dropwise and the resulting slurry is stirred for 16 hours. The solvents are removed in vacuo and the residue is dissolved in 150 ml each of methyl-t-butyl ether and 1M NaHSO$_4$. The phases are separated and the organic layer is washed with 150 ml each of water and saturated aqueous sodium chloride. The organic layer is dried over sodium sulfate, filtered and concentrated in vacuo to give 9.67 g of 3,4-dichlorophenyl methylsulfide (90%).

The sulfide from above is converted to the corresponding sulfone as described below for Amine 38. The 3,4 dichloromethyl sulfone is coupled to 4-(2-amino-2-methylpropyl) phenol to prepare the title amine by a procedure substantially similar to that described above for Amine 4.

Amine 31

To a 1 gallon autoclave is added 2,5-dichloropyridine (123 g, 830 mmol), palladium II acetate (5.6 g, 24.9 mmol), 1,3-bis(diphenylphosphine)propane (20.5 g, 49.8 mmol), 1,1,1,3,3,3,-hexamethyldisilazane (700 ml), acetonitrile (1180 ml) and dimethylformamide (295 ml). The autoclave is pressurized to 70 psi with carbon monoxide and heated to 80° C. for 16 hours. The reaction mixture is filtered and washed with acetonitrile. The mixture is concentrated in vacuo to 590 g and 1 L of water is added. The resulting slurry is cooled to 0° C. and filtered to give 102.6 g (79%) of 2-carboxamido-5-chloropyridine which is used without further purification.

2-Carboxamido-5-chloropyridine is coupled to 4-(2-amino-2-methylpropyl)phenol to prepare the title Amine by a procedure substantially similar to that described above for Amine 4.

Amine 36

Oxalyl chloride (18.1 ml, 207 mmol) is added slowly to dimethylformamide cooled to −25° C. The resulting mixture is cooled to −45° C. and 2-carboxamido-5-chloropyridine (25 g, 160 mmol) is added portionwise. The reaction stirred for 30 minutes and pyridine (14.2 ml, 176 mmol) is added. The reaction stirred for 5 hours, 20 minutes and is poured into 1.5 L of water and 1 L of ethyl acetate is added. The phases are separated and the aqueous layer is extracted with 100 ml of ethyl acetate. The combined organics are washed with water (850 ml and 350 ml), saturated aqueous sodium chloride (100 ml), dried over sodium sulfate, filtered and concentrated in vacuo to give 19.95 g (92%) of 2-cyano-5-chloropyridine which is used without further purification.

2-Cyano-5-chloropyridine is coupled to 4-(2-amino-2-methylpropyl)phenol to prepare the title amine by a procedure substantially similar to that described above for Amine 4.

Amine 38

To a solution of n-butyl lithium (0.544 mol) in tetrahydrofuran (700 ml) at −78° C. is added a solution of 3,4- difluorobromobenzene (100 g, 0.518 mol) in 200 ml of tetrahydrofuran. After 10 minutes, a solution of dimethyl disulfide in 100 ml of tetrahydrofuran is added and the resulting reaction mixture is warmed to ambient temperature over 60 minutes. The reaction is concentrated in vacuo and the resulting oil is partitioned between 750 ml methyl-t-butyl ether and 300 ml water. The phases are separated and the organic layer is washed with 300 ml of saturated aqueous sodium chloride, dried over magnesium sulfate, filtered, and concentrated in vacuo. The resulting oil is purified by vacuum distillation to provide 43.08 g of 3,4-difluorophenyl methylsulfide.

Metachloroperbenzoic acid (60.4 mmol) is added portion-wise to a solution of the sulfide (43 g, 26.8 mmol) in 1 L of dichloromethane at 0° C. After 15 minutes, the reaction mixture is warmed to ambient temperature and stirred for 1.25 hours. The solids are removed by filtration and the resulting solution washed with 750 ml of 1M sodium bisulfite, 2 L sodium bicarbonate, 1 L water, and 750 ml saturated aqueous sodium chloride. The organic layer is dried over magnesium sulfate, filtered and concentrated in vacuo to give 45.17 g (88%) of the title amine.

Amine 41

The acetic acid salt of 4-(2-amino-2-methylpropyl)phenol (15 g, 66.5 mmol) is dissolved in 90 ml of hot water. 5N aqueous sodium hydroxide (13.98 ml, 0.0699 mol) is added and the resulting mixture is allowed to stir for one hour upon which a precipitate formed. The reaction is then placed in the refrigerator to allow more precipitation. The precipitate is filtered to afford 6.91 g of 4-(2-amino-2-methylpropyl) phenol free base.

4-(2-Amino-2-methylpropyl)phenol free base (6.91 g, 41.8 mmol) is dissolved in 100 ml of anhydrous tetrahydrofuran and the solution is purged with nitrogen. Di-t-butyl-dicarbonate (10.56 ml, 46 mmol) is added and the resulting solution is allowed to stir overnight. The reaction is concentrated, the residue dissolved in ethyl acetate, and then washed with water. The organic layer is dried over sodium sulfate, filtered and concentrated to a clear oil. The oil is taken up in anhydrous tetrahydrofuran and diisopropylethylamine (7.94 ml, 46 mmol) is added followed by trifluoromethanesulfonic anhydride (7.67 ml, 45 mmol). The reaction is allowed to stir for 3 hours, quenched with water, extracted with ethyl acetate, dried over sodium sulfate and concentrated to a clear solid.

A portion of the above solid (2.7 g, 6.8 mmol) is mixed with 3-cyanophenyl boronic acid (1.0 g, 6.8 mmol), aqueous potassium carbonate (2M, 7.1 ml, 14.3 mmol), lithium chloride (288 mg, 6.8 mmol) and 60 ml of tetrahydrofuran. The reaction is fitted with a condensor and purged with nitrogen before palladium(0) tetrakistriphenylphoshine is added (37.9 mg, 0.34 mmol). The reaction flask is covered with aluminum foil and the solution is brought to reflux. After 16 hours, the reaction is poured into a separatory funnel. Ethyl acetate (100 ml) is added and the organic layer is washed with water, 1N aqueous HCl, water, 1N aqueous sodium hydroxide and again with water. The organic layer is dried over sodium sulfate and concentrated to a brown solid. The crude product is purified on a silica flash column eluting with 20% ethyl acetate/80% hexanes to give 900 mg of the amine protected title amine.

The protected amine from above (1.025 g, 2.9 mmol) is placed in a flask and stirred with trifluoroacetic acid (neat). After 10 minutes, the solution is concentrated and taken up in 10 ml of methanol. This solution is then placed on a 10 g SCX column and washed with methanol (2×10 ml). The product is eluted with methanolic ammonia (2M) to give 735 mg of the title amine.

Amine 43

Carbonyldiimidazole (43.0 g, 265 mmol) is added in one portion to a solution of 2-chloro-5-carboxythiophene (39.2 g, 241 mmol) in 400 ml of tetrahydrofuran. The resulting mixture is allowed to stir for 60 minutes before aqueous ammonium hydroxide (28%, 125 ml) is added in one portion. After stirring for 90 minutes, the mixture is concentrated in vacuo and the residue is dissolved in ethyl acetate (750 ml). This organic solution is washed with aqueous sodium hydroxide (1N, 100 ml) and then four times with aqueous hydrochloric acid (1N, 100 ml). The organic layer is dried over sodium sulfate, filtered, and concentrated in vacuo, and dried overnight at 40° C. in vacuo to give 22.6 g of 2-chloro-5-carboxamidothiophene.

Oxalyl chloride (8.9 ml, 102 mmol) is added dropwise to a cold solution (−40° C.) of 2-chloro-5-carboxamidothiophene (15 g, 92.8 mmol) in dimethylformamide (150 ml). After the addition is complete, the reaction is allowed to stir for 2 hours before it is diluted with ethyl acetate (500 ml). The resulting mixture is washed four times with water (25 ml), dried over sodium sulfate, and concentrated in vacuo to give 12.3 g of 2-chloro-5-cyanothiophene.

2-Chloro-5-cyanothiophene (3.8 g, 26.6 mmol) and 4-(2-amino-2-methylpropyl)phenol (4.0 g, 17.8 mmol) are dissolved in dimethylsulfoxide (15 ml). Sodium hydride (60% dispersion in oil, 1.5 g) is added in portions over 2 hours. The first addition (about half of the total) is done at room temperature. The reaction is heated to 50° C. and the remaining sodium hydride is added in portions. After the additions are complete, the reaction mixture is heated to 90° C. and is allowed to stir for 44 hours. After allowing the reaction mixture to cool, it is diluted with dichloromethane (45 ml) and water (90 ml). The layers are separated and the organic layer is washed with water (15 ml). Water (77 ml) is added to the organic layer and the pH of the aqueous phase is adjusted to 1 with concentrated hydrochloric acid (1.9 ml). The aqueous layer is washed with dichloromethane (14 ml) and then the pH is adjusted to 13 with aqueous sodium hydroxide (5N, 14 ml). The aqueous layer is extracted three times with dichloromethane (90 ml, 2×45 ml). The extracts are combined, dried over sodium sulfate, and concentrated in vacuo to give 3.5 g of the title amine.

Amine 48

2-Methyl-hydroxy-phenol (15.0 g, 0.12 mol), 2-nitro propane (60.8 ml, 676 mmol), potassium t-butoxide (6.77 g, 60 mmol) and diglyme (150 ml) are mixed together in a reaction vessel and said vessel is fitted with a Dean-Stark water trap. The reaction is heated to 134° C. until water and solvent began to collect in the trap. The reaction is slowly heated to 149° C. and then is allowed to cool back down to 130° C. at which point the reaction is stirred for 3 hours. Reaction is cooled to room temperature and water (20 ml) is added. After concentrating to about half the volume, water (100 ml) is added and the mixture is extracted with ethyl acetate (2×100 ml). The organic layer is then washed with 1N aqueous hydrochloric acid and water, dried over sodium sulfate and concentrated to a brown oil. A mixture of ethyl acetate and hexanes, (300 ml, 1:4 ethyl acetate/hexanes) is added and product is triturated.

The product from above (7.0 g) is taken up in methanol and acetic acid and 5% palladium on carbon is added.

Hydrogen gas is injected into the reaction vessel up to 50 p.s.i. The mixture is then heated to 50° C. and shaken for 16 hours. The catalyst is filtered and the reaction is concentrated. Ethyl acetate (400 ml) is added and product is filtered to give 7.55 g of 2-(2-amino-2-methylpropyl)phenol acetic acid salt. 2-(Amino-2-methylpropyl)phenol acetic acid salt is converted to its free base form, the free base is reacted with di-t-butyl-dicarbonate, and the protected amine is reacted with 4-cyanophenyl boronic acid to prepare the title amine substantially as described above for Amine 41.

Amines 5, 13–23, 25, 28, 30, 32, 34, 35, 37, 39, 42, 44–47 and 49

Amines 5, 13–23, 25, 28, 30, 32, 34, 35, 37 and 39 are prepared by procedures substantially similar to that described for Amine 4. Amines 42 and 47 are prepared by procedures substantially similar to that described for Amine 41. Amines 44–46 are prepared by procedures substantially similar to that described for Amine 43. Amine 49 is prepares by procedures substantially similar to that described for Amine 48.

Aryl Halides of Formula V

Aryl halides 1–14 are prepared for use as described in Scheme 2. These aryl halides are pictured below in Tables 6 and 7.

TABLE 6

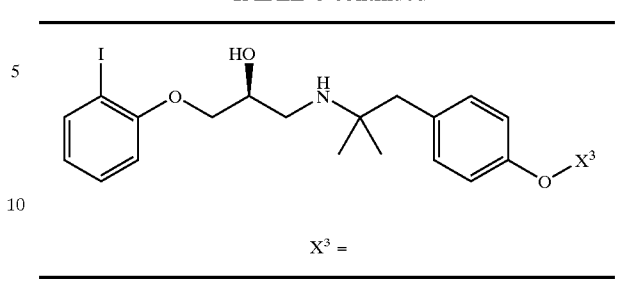

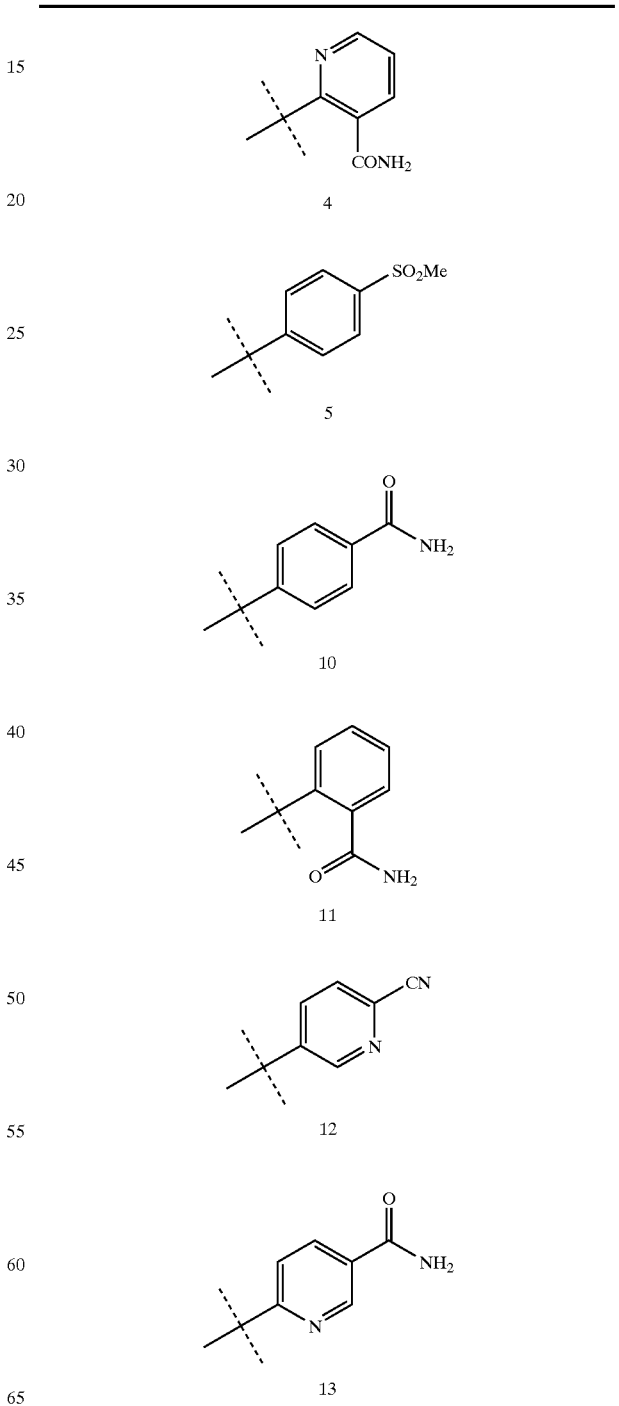

TABLE 6-continued

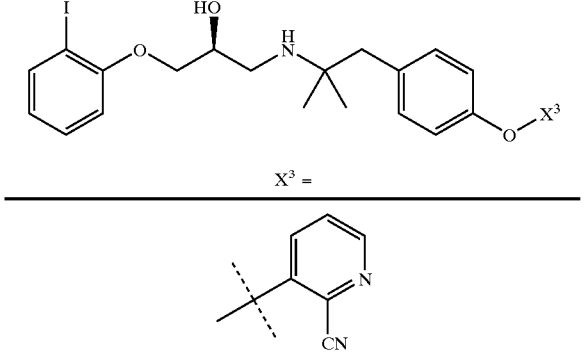

X³ =

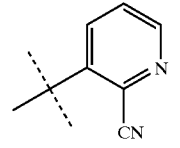

14

TABLE 7

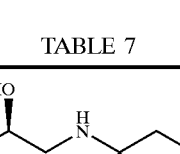

X³ =

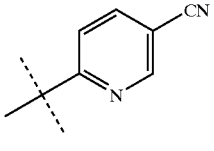

6

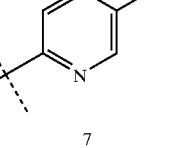

7

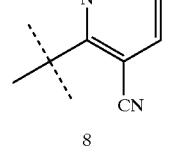

8

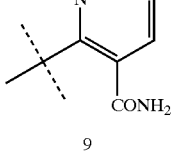

9

Representative Procedure 1: Preparation of Aryl Halides (2S)-1-(2-iodophenyloxy)-2,3-epoxypropane (Epoxide 22, 8 mmol) or (2S)-1-(2-iodo-6-fluorophenyloxy)-2,3-epoxypropane (Epoxide 55) is reacted with an equimolar amount of an amine of formula III (Amines 2–5, 9, 10, 12, 31, 36 or 40) in 100 ml of refluxing dry ethanol overnight. After evaporation of the solvent the residue is purified via flash chromatography on silica gel using a dichloromethane-dichloromethane/ethanolic ammonia gradient (100 to 95:5).

Boronic Acids

The following boronic acids or cyclic esters are obtained from commercial sources for use as described in Scheme 2.

TABLE 8

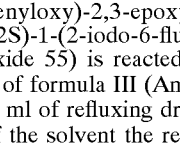

1

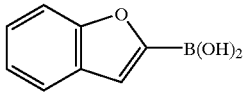

2

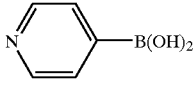

3

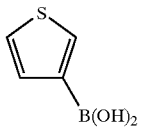

4

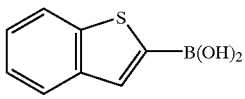

5

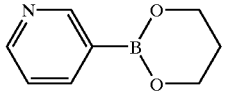

6

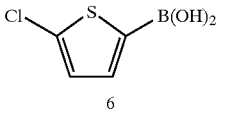

7

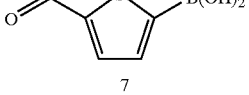

8

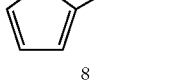

9

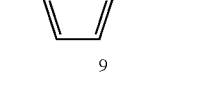

10

EXAMPLES

Representative Procedure 2: Amination of Epoxide

A vial is charged with a solution of single amine of formula III (0.2M in ethanol or t-butanol, 90 micromolar) and a solution of a single epoxide of formula II (0.2M in dimethylsulfoxide, 80 micromolar). The vial is sealed and heated to 80° C. for 24–48 hours. The solution is cooled to room temperature, diluted with methanol, and passed over a cation exchange column, eluting the basic material with 1N methanolic ammonia.

Representative Procedure 3: Amination of Epoxide

A stirred mixture of an epoxide of formula II (1 equivalent) and an amine of formula III (1–2 equivalents) in ethanol, methanol, n-butanol or t-butanol is heated at 70–80° C. for 2–72 hours. The solvent is evaporated to dryness to give a crude oil that is optionally diluted with methanol or ethanol and passed over a cation exchange column (eluting the free base product with 1N methanolic ammonia) before further purification.

The final products prepared via Representative Procedure 2 or 3 may be further purified by flash or radial chromatography. Typical chromatography conditions include: a) using a variable mixture of 25:5:1 chloroform/methanol/ammonium hydroxide and 9:1 chloroform/methanol; b) a variable mixture of 90:10:1 $CH_2Cl_2$/ethanolic $NH_3$ gradient; c) dichloromethane/6–12% methanol, 0.15–0.35M ammonia in dichloromethane gradient; d) methylene chloride with a step gradient to 2–8% methanol; e) chloroform/2.0M ammonia in methanol, from 0–10% to 6–20% gradient elution or f) isocratic 6–8% 2M ammonia in methanol: 92–94% dichloromethane.

Alternatively, the final products may be purified on C18 bonded silica gel using either mass guided or UV guided reverse phase liquid chromatography (acetonitrile/water with 0.01% hydrochloric acid or 0.1% trifluoroacetic acid). When purification of a compound of the present invention results in production of a free base, the free base thus prepared may be salified, e.g., by dissolution of the free base in $CH_2Cl_2$ or diethylether, adding 1M ethanolic HCl or a solution of HCl in diethylether, and evaporating the volatiles, or as described in more detail below.

For example, a hydrochloride salt may be prepared by dissolving the free base in dichloromethane, diethylether, or a mixture of ethyl acetate and methanol and adding 1M ethanolic HCl, a solution of HCl in diethylether, or 0.5M ammonium chloride. The resulting mixture is allowed to stir for a short time, e.g., for five minutes, before evaporating the volatiles and optionally triturating in diethyl ether to give the hydrochloride salt.

The oxalate salts may be prepared by dissolving the free base in a small amount of ethyl acetate, optionally adding methanol for solubility. The resulting solution is treated with 1 equivalent of a 0.5M solution of oxalic acid in ethyl acetate. The reaction mixture is either concentrated in vacuo or centrifuged, separated, and the solids are dried, to give the oxalate salt.

To prepare a succinate salt, the free base may be dissolved in a small amount of ethyl acetate or methanol and then treated with 1 equivalent of succinic acid in methanol. The resulting slurry is dissolved in the minimum amount of methanol then concentrated in vacuo to give the succinate salt.

For products synthesized from Epoxide 6, the crude products are treated with 1N HCl/dioxane for 2 hours at room temperature and concentrated before purifying on C18 bonded silica gel as described above to give a compound of the formula:

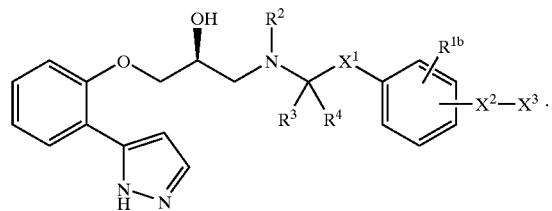

For products synthesized from Epoxide 20, the title compounds are prepared by removal of the Boc-protecting group from the imidazoline ring by stirring a solution of the crude protected product in dichloromethane/2N HCl 10:1.

For products synthesized from Epoxide 24, the intermediate N,N-dimethylamino-propenones are treated with hydrazine hydrate in ethanol to give a compound of the formula:

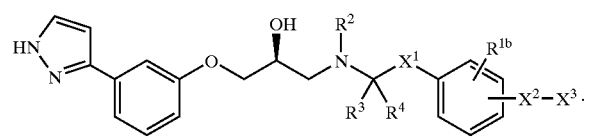

The table below sets out representative combinations of Amines and Epoxides that are reacted as described above in Representative Procedure 2 or 3. Preparation of desired product is confirmed via mass spectral analysis (MSA). Emax±Standard Error Mean (SEM) data, discussed in the "Demonstration of Function" section below, is also included for said compounds where available. The Emax values represent the average of at least 3 runs except as otherwise indicated.

TABLE 9

| E.g. | Epoxide | Amine | MSA | Isolated Form | Emax (%) ± SEM |
|---|---|---|---|---|---|
| 1 | 3 | 1 | 475.2 | Trifluoro Acetate | 58.1 ± 2.6 |
| 2 | 5 | 1 | 460.2 | Trifluoro Acetate | 43.6 ± 9.7 |
| 3 | 1 | 2 | 498.3 | Free Base | <10 |
| 4 | 2 | 4 | 498.3 | Free Base | 55.0 ± 1.3 |
| 5 | 3 | 2 | 500.3 | Free Base | 66.1 ± 4.8 |
| 6 | 4 | 2 | 501.3 | Free Base | 58.7 ± 1.8 |
| 7 | 5 | 2 | 485.0 | Free Base | 48.8 ± 2.5 |
| 8 | 6 | 2 | 484.1 | Free Base | 33.7 ± n = 1 |
| 9 | 7 | 2 | 533.4 | Free Base | 23.7 ± 10.0 |
| 10 | 8 | 2 | 496.6 | Free Base | 35.1 ± 0.9 |
| 11 | 9 | 2 | 501.4 | Free Base | 18.0 ± 6.5 |
| 12 | 21 | 2 | 485.2 | Hydrochloride | 64.8 ± 6.3 |
| 13 | 33 | 2 | 485.3 | Hydrochloride | 54.8 ± 1.7 |
| 14 | 1 | 3 | 516.3 | Free Base | 16.9 ± n = 1 |
| 15 | 2 | 5 | 516.3 | Free Base | 70.9 ± 3.0 |
| 16 | 3 | 3 | 518.3 | Free Base | 67.6 ± 4.7 |
| 17 | 4 | 3 | 519.3 | Free Base | 62.9 ± 2.2 |
| 18 | 5 | 3 | 503.0 | Free Base | 49.1 ± 2.9 |
| 19 | 6 | 3 | 502.1 | Free Base | 31.3 ± n = 1 |
| 20 | 7 | 3 | 551.5 | Free Base | 30.4 ± 2.5 |
| 21 | 7 | 5 | 551.4 | Free Base | 48.0 ± 2.0 |
| 22 | 9 | 3 | 519.3 | Free Base | 22.0 ± 5.3 |
| 23 | 10 | 3 | 521.4 | Di-Hydrochloride | 29.9 ± 3.2 |
| 24 | 11 | 3 | 519.5 | Di-Hydrochloride | 17.3 ± 3.2 |
| 25 | 12 | 3 | 520.4 | Tri-Hydrochloride | 13.7 ± 3.5 |
| 26 | 13 | 3 | 553.3 | Free Base | 41.4 ± 6.6 |
| 27 | 14 | 3 | 569.3 | Free Base | 20.8 ± 8.5 |
| 28 | 15 | 3 | 533.3 | Free Base | 83.4 ± 7.2 |
| 29 | 17 | 3 | 501.3 | Hydrochloride | 48.4 ± 5.9 |
| 30 | 18 | 3 | 504.5 | Free Base | 51.7 ± 2.7 |
| 31 | 19 | 3 | 538.3 | Free Base | 12.1 ± n = 1 |
| 32 | 21 | 3 | 503.3 | Hydrochloride | 54.2 ± 5.0 |

TABLE 9-continued

| E.g. | Epoxide | Amine | MSA | Isolated Form | Emax (%) ± SEM |
|---|---|---|---|---|---|
| 33 | 23 | 3 | 529.3 | Free Base | 26.2 ± 4.3 |
| 34 | 24 | 3 | 502.4 | Free Base | <10 |
| 35 | 25 | 3 | 503.3 | Free Base | 28.9 ± n = 1 |
| 36 | 37 | 3 | 503.3 | Free Base | 17.5 ± n = 1 |
| 37 | 5 | 3 | 489.2 | Trifluoro Acetate | 41.5 ± 0.5 |
| 38 | 26 | 3 | 529.3 | Free Base | 20.5 ± n = 1 |
| 39 | 27 | 3 | 519.2 | Oxalate | 67.1 ± 0.7 |
| 40 | 27 | 3 | 500.3 | Trifluoro Acetate | 79.5 ± 6.7 |
| 41 | 38 | 3 | 518.3 | Hydrochloride | 33.5 ± 4.2 |
| 42 | 28 | 3 | 520.2 | Oxalate | 43.3 ± 2.7 |
| 43 | 40 | 3 | 502.4 | Hydrochloride | 61.9 ± 2.5 |
| 44 | 29 | 3 | 520.2 | Oxalate | 22.1 ± 3.3 |
| 45 | 32 | 3 | 503.3 | Free Base | 66.5 ± 3.9 |
| 46 | 33 | 3 | 503.3 | Hydrochloride | 64.7 ± 1.3 |
| 47 | 34 | 3 | 502.4 | Hydrochloride | 35.5 ± 5.5 |
| 48 | 1 | 4 | 498.3 | Free Base | 14.4 ± n = 1 |
| 49 | 2 | 2 | 498.3 | Free Base | 59.1 ± n = 1 |
| 50 | 3 | 4 | 500.3 | Free Base | 78.9 ± 2.5 |
| 51 | 3 | 4 | 499.9 | Hydrochloride | 74.1 ± 3.3 |
| 52 | 4 | 4 | 501.3 | Free Base | 70.1 ± 3.3 |
| 53 | 5 | 4 | 485.0 | Free Base | 74.5 ± 12.5 |
| 54 | 5 | 4 | 484.9 | Hydrochloride | 66.8 ± 6.8 |
| 55 | 6 | 4 | 484.1 | Free Base | 37.5 ± n = 1 |
| 56 | 7 | 4 | 533.3 | Free Base | 30.1 ± 2.1 |
| 57 | 8 | 4 | 496.4 | Free Base | 41.8 ± 5.6 |
| 58 | 9 | 4 | 501.3 | Free Base | 21.0 ± 3.4 |
| 59 | 20 | 3 | 504.3 | Free Base | <10 |
| 60 | 21 | 4 | 485.2 | Hydrochloride | 70.8 ± 3.1 |
| 61 | 23 | 4 | 511.4 | Free Base | 32.8 ± 4.3 |
| 62 | 37 | 4 | 485.3 | Trifluoro Acetate | 24.7 ± 5.2 |
| 63 | 30 | 4 | 518.2 | Oxalate | 52.6 ± 2.5 |
| 64 | 31 | 4 | 518.2 | Trifluoro Acetate | 30.5 ± 6.8 |
| 65 | 33 | 4 | 485.3 | Hydrochloride | 55.9 ± 5.8 |
| 66 | 1 | 5 | 516.3 | Free Base | 26.6 ± n = 1 |
| 67 | 2 | 3 | 516.3 | Free Base | 77.4 ± n = 1 |
| 68 | 3 | 5 | 518.3 | Free Base | 83.7 ± 3.0 |
| 69 | 3 | 5 | 517.9 | Hydrochloride | 80.7 ± 4.4 |
| 70 | 4 | 5 | 519.3 | Free Base | 73.8 ± 6.0 |
| 71 | 4 | 5 | 518.9 | Hydrochloride | 65.6 ± 1.3 |
| 72 | 5 | 5 | 503.0 | Free Base | 67.6 ± 7.1 |
| 73 | 5 | 5 | 502.9 | Hydrochloride | 69.5 ± 0.1 |
| 74 | 6 | 5 | 502.1 | Free Base | 36.8 ± n = 1 |
| 75 | 8 | 3 | 514.5 | Free Base | 40.3 ± 3.7 |
| 76 | 8 | 5 | 514.3 | Free Base | 48.8 ± 5.5 |
| 77 | 9 | 5 | 519.3 | Free Base | 22.4 ± 4.6 |
| 78 | 10 | 5 | 521.4 | Di-Hydrochloride | 30.3 ± 5.1 |
| 79 | 11 | 5 | 519.3 | Di-Hydrochloride | 21.3 ± 3.3 |
| 80 | 12 | 5 | 520.4 | Tri-Hydrochloride | 12.3 ± 0.2 |
| 81 | 13 | 5 | 553.3 | Free Base | 60.4 ± 5.1 |
| 82 | 14 | 5 | 569.2 | Free Base | 45.9 ± 10.7 |
| 83 | 15 | 5 | 533.3 | Hydrochloride | 83.5 ± 4.4 |
| 84 | 16 | 5 | 505.3 | Free Base | 72.1 ± 6.2 |
| 85 | 17 | 5 | 501.2 | Hydrochloride | 69.2 ± 12.1 |
| 86 | 18 | 5 | 504.3 | Free Base | 64.6 ± 3.3 |
| 87 | 19 | 5 | 538.1 | Free Base | 14.2 ± n = 1 |
| 88 | 20 | 5 | 504.3 | Free Base | <10 |
| 89 | 21 | 5 | 503.3 | Hydrochloride | 71.8 ± 2.5 |
| 90 | 23 | 5 | 529.5 | Free Base | 31.5 ± 2.8 |
| 91 | 26 | 5 | 529.3 | Free Base | 24.9 ± 9.3 |
| 92 | 24 | 5 | 502.4 | Free Base | 14.4 ± n = 1 |
| 93 | 25 | 5 | 503.3 | Free Base | <10 |
| 94 | 37 | 5 | 503.3 | Free Base | <10 |
| 95 | 39 | 5 | 536.3 | Hydrochloride | 13.9 ± 0.1 |
| 96 | 27 | 5 | 519.2 | Oxalate | 78.1 ± 6.6 |
| 97 | 28 | 5 | 520.2 | Oxalate | 52.4 ± 0.8 |
| 98 | 29 | 5 | 520.2 | Oxalate | 39.2 ± 4.0 |
| 99 | 30 | 5 | 536.2 | Oxalate | 59.1 ± 0.6 |
| 100 | 31 | 5 | 536.2 | Trifluoro Acetate | 31.4 ± 5.0 |
| 101 | 33 | 5 | 503.3 | Hydrochloride | 67.4 ± 4.0 |
| 102 | 34 | 5 | 502.4 | Hydrochloride | 46.1 ± 4.5 |
| 103 | 35 | 5 | 520.5 | Free Base | 21.1 ± 0.1 |
| 104 | 36 | 5 | 502.4 | Hydrochloride | 36.0 ± 5.0 |
| 105 | 1 | 6 | 545.4 | Free Base | <10 |
| 106 | 2 | 6 | 545.3 | Free Base | 53.2 ± 2.4 |
| 107 | 3 | 6 | 547.3 | Free Base | 84.3 ± 5.3 |
| 108 | 3 | 6 | 547.2 | Trifluoro Acetate | 87.7 ± 11.9 |
| 109 | 4 | 6 | 548.3 | Free Base | 61.4 ± 4.4 |
| 110 | 5 | 6 | 532.0 | Free Base | 60.3 ± 3.9 |
| 111 | 6 | 6 | 531.1 | Free Base | 23.6 ± n = 1 |
| 112 | 5 | 6 | 532.2 | Trifluoro Acetate | 56.9 ± 8.6 |
| 113 | 1 | 7 | 531.3 | Free Base | 20.7 ± n = 1 |
| 114 | 2 | 7 | 531.3 | Free Base | 56.6 ± n = 1 |
| 115 | 3 | 7 | 533.3 | Free Base | 61.9 ± 7.0 |
| 116 | 4 | 7 | 534.3 | Free Base | 58.2 ± 7.2 |
| 117 | 5 | 7 | 518.0 | Free Base | 32.2 ± 6.5 |
| 118 | 6 | 7 | 517.1 | Free Base | 29.5 ± n = 1 |
| 119 | 3 | 8 | 499.2 | Trifluoro Acetate | 55.2 ± 3.6 |
| 120 | 4 | 8 | 500.2 | Trifluoro Acetate | 35.8 ± 4.6 |
| 121 | 5 | 8 | 484.3 | Trifluoro Acetate | 38.9 ± 7.1 |
| 122 | 27 | 8 | 505.3 | Trifluoro Acetate | 61.9 ± 5.3 |
| 123 | 3 | 9 | 516.2 | Trifluoro Acetate | 73.6 ± 8.2 |
| 124 | 4 | 9 | 518.2 | Trifluoro Acetate | 46.7 ± 3.6 |
| 125 | 5 | 9 | 502.2 | Trifluoro Acetate | 40.3 ± 7.9 |
| 126 | 27 | 9 | 518.2 | Trifluoro Acetate | 62.2 ± 1.3 |
| 127 | 1 | 10 | 550.3 | Free Base | <10 |
| 128 | 2 | 10 | 550.3 | Free Base | 40.6 ± n = 1 |
| 129 | 3 | 10 | 552.2 | Trifluoro Acetate | 53.2 ± 4.8 |
| 130 | 4 | 10 | 553.3 | Free Base | 49.5 ± 3.4 |
| 131 | 4 | 10 | 552.9 | Trifluoro Acetate | 43.5 ± 1.4 |
| 132 | 5 | 10 | 537.0 | Free Base | 34.6 ± 7.8 |
| 133 | 6 | 10 | 536.1 | Free Base | 21.4 ± n = 1 |
| 134 | 21 | 10 | 537.4 | Hydrochloride | 47.7 ± 6.5 |
| 135 | 5 | 10 | 537.2 | Trifluoro Acetate | 35.2 ± 4.3 |
| 136 | 39 | 10 | 570.2 | Hydrochloride | <10 |
| 137 | 1 | 11 | 564.3 | Free Base | <10 |
| 138 | 2 | 11 | 564.3 | Free Base | 41.7 ± n = 1 |
| 139 | 3 | 11 | 566.3 | Free Base | 62.2 ± 7.4 |
| 140 | 4 | 11 | 567.3 | Free Base | 48.9 ± 2.5 |
| 141 | 5 | 11 | 551.0 | Free Base | 48.3 ± 9.9 |
| 142 | 6 | 11 | 550.1 | Free Base | 20.2 ± n = 1 |
| 143 | 3 | 12 | 500.2 | Trifluoro Acetate | 67.2 ± 4.8 |
| 144 | 4 | 12 | 501.2 | Trifluoro Acetate | 55.9 ± 1.1 |
| 145 | 4 | 36 | 501.2 | Trifluoro Acetate | 44.6 ± 6.2 |
| 146 | 5 | 12 | 484.2 | Trifluoro Acetate | 58.7 ± 2.9 |
| 147 | 27 | 12 | 501.2 | Trifluoro Acetate | 58.9 ± 3.6 |
| 148 | 30 | 12 | 536.2 | Trifluoro Acetate | 51.6 ± 9.7 |
| 149 | 31 | 12 | 518.2 | Trifluoro Acetate | 26.9 ± 4.0 |
| 150 | 3 | 13 | 476.2 | Trifluoro Acetate | 69.8 ± 6.0 |
| 151 | 4 | 13 | 477.2 | Trifluoro Acetate | 73.1 ± 3.8 |
| 152 | 5 | 13 | 461.2 | Trifluoro Acetate | 45.3 ± 4.2 |
| 153 | 3 | 14 | 476.2 | Trifluoro Acetate | 66.8 ± 5.5 |
| 154 | 4 | 14 | 477.3 | Trifluoro Acetate | 61.1 ± 7.7 |
| 155 | 5 | 14 | 461.2 | Trifluoro Acetate | 46.6 ± 4.2 |
| 156 | 3 | 15 | 577.1 | Trifluoro Acetate | 84.9 ± 0.2 |
| 157 | 4 | 15 | 578.1 | Trifluoro Acetate | 73.3 ± 6.6 |
| 158 | 5 | 15 | 562.1 | Trifluoro Acetate | 73.0 ± 3.0 |
| 159 | 3 | 16 | 577.1 | Trifluoro Acetate | 76.9 ± 7.4 |
| 160 | 5 | 16 | 562.2 | Trifluoro Acetate | 56.3 ± 1.4 |
| 161 | 3 | 17 | 533.2 | Trifluoro Acetate | 52.5 ± 4.7 |
| 162 | 4 | 17 | 428.2 | Trifluoro Acetate | 36.2 ± 2.6 |
| 163 | 5 | 17 | 518.2 | Trifluoro Acetate | 44.6 ± 4.3 |
| 164 | 3 | 18 | 551.2 | Trifluoro Acetate | 67.3 ± 3.5 |
| 165 | 4 | 18 | 552.2 | Trifluoro Acetate | 49.7 ± 3.9 |
| 166 | 5 | 18 | 536.2 | Trifluoro Acetate | 58.3 ± 9.5 |
| 167 | 3 | 19 | 509.2 | Trifluoro Acetate | 57.3 ± 3.5 |
| 168 | 4 | 19 | 510.2 | Trifluoro Acetate | 56.1 ± 4.5 |
| 169 | 5 | 19 | 494.2 | Trifluoro Acetate | 43.3 ± 6.8 |
| 170 | 3 | 20 | 576.2 | Trifluoro Acetate | 55.0 ± 4.8 |
| 171 | 4 | 20 | * | Trifluoro Acetate | 47.9 ± 6.5 |
| 172 | 5 | 20 | 561.2 | Trifluoro Acetate | 40.4 ± 8.8 |
| 173 | 3 | 21 | 543.2 | Trifluoro Acetate | 87.9 ± 4.5 |
| 174 | 5 | 21 | 528.2 | Trifluoro Acetate | 59.3 ± 3.2 |
| 175 | 3 | 22 | 509.2 | Trifluoro Acetate | 67.4 ± 3.9 |
| 176 | 4 | 22 | 510.2 | Trifluoro Acetate | 57.0 ± 7.6 |
| 177 | 5 | 22 | 494.2 | Trifluoro Acetate | 46.0 ± 1.7 |
| 178 | 3 | 23 | 509.2 | Trifluoro Acetate | 64.4 ± 5.2 |
| 179 | 4 | 23 | 510.2 | Trifluoro Acetate | 62.2 ± 8.6 |
| 180 | 5 | 23 | 494.2 | Trifluoro Acetate | 52.4 ± 6.9 |
| 181 | 3 | 24 | 586.2 | Trifluoro Acetate | 66.2 ± 1.6 |
| 182 | 4 | 24 | 587.1 | Trifluoro Acetate | 57.6 ± 7.1 |
| 183 | 5 | 24 | 571.2 | Trifluoro Acetate | 53.7 ± 4.3 |
| 184 | 3 | 25 | 564.2 | Trifluoro Acetate | 64.1 ± 3.2 |

TABLE 9-continued

| E.g. | Epoxide | Amine | MSA | Isolated Form | Emax (%) ± SEM |
|---|---|---|---|---|---|
| 185 | 4 | 25 | 565.2 | Trifluoro Acetate | 45.1 ± 2.6 |
| 186 | 5 | 25 | 549.2 | Trifluoro Acetate | 41.1 ± 8.2 |
| 187 | 3 | 26 | 517.2 | Trifluoro Acetate | 45.1 ± 1.5 |
| 188 | 4 | 26 | 518.2 | Trifluoro Acetate | 38.3 ± 5.7 |
| 189 | 5 | 26 | 502.2 | Trifluoro Acetate | 35.1 ± 5.2 |
| 190 | 3 | 27 | 535.2 | Trifluoro Acetate | 54.5 ± 3.3 |
| 191 | 4 | 27 | 536.2 | Trifluoro Acetate | 49.5 ± 1.5 |
| 192 | 5 | 27 | 520.2 | Trifluoro Acetate | 40.3 ± 6.9 |
| 193 | 3 | 28 | 543.2 | Trifluoro Acetate | 73.5 ± 3.2 |
| 194 | 4 | 28 | 544.2 | Trifluoro Acetate | 56.6 ± 4.2 |
| 195 | 5 | 28 | 528.2 | Trifluoro Acetate | 48.1 ± 3.8 |
| 196 | 3 | 29 | 518.2 | Trifluoro Acetate | 74.4 ± 3.3 |
| 197 | 4 | 29 | 519.2 | Trifluoro Acetate | 67.7 ± 2.7 |
| 198 | 5 | 29 | 503.2 | Trifluoro Acetate | 48.1 ± 6.5 |
| 199 | 27 | 29 | 519.3 | Trifluoro Acetate | 83.0 ± 4.0 |
| 200 | 30 | 29 | 518.2 | Trifluoro Acetate | 59.5 ± 3.7 |
| 201 | 31 | 29 | 517.2 | Trifluoro Acetate | 26.8 ± 4.2 |
| 202 | 3 | 30 | 475.2 | Trifluoro Acetate | 59.1 ± 6.0 |
| 203 | 4 | 30 | 476.2 | Trifluoro Acetate | 57.8 ± 3.1 |
| 204 | 3 | 37 | 580.2 | Trifluoro Acetate | 67.6 ± 4.0 |
| 205 | 3 | 31 | 518.2 | Trifluoro Acetate | 70.3 ± 0.3 |
| 206 | 4 | 31 | 519.2 | Trifluoro Acetate | 64.2 ± 8.1 |
| 207 | 27 | 31 | 519.2 | Trifluoro Acetate | 70.5 ± 4.9 |
| 208 | 3 | 32 | 510.2 | Trifluoro Acetate | 92.4 ± 7.3 |
| 209 | 4 | 32 | 511.2 | Trifluoro Acetate | 88.3 ± 8.0 |
| 210 | 5 | 32 | * | Trifluoro Acetate | 89.1 ± 2.7 |
| 211 | 27 | 32 | 511.2 | Trifluoro Acetate | 88.5 ± 9.3 |
| 212 | 5 | 33 | 484.7 | Trifluoro Acetate | 68.9 ± 3.1 |
| 213 | 27 | 33 | 500.2 | Trifluoro Acetate | 63.0 ± 3.2 |
| 214 | 30 | 33 | 517.2 | Trifluoro Acetate | 42.4 ± 9.4 |
| 215 | 31 | 33 | 535.2 | Trifluoro Acetate | 28.1 ± 4.5 |
| 216 | 3 | 34 | 533.2 | Trifluoro Acetate | 85.4 ± 4.9 |
| 217 | 5 | 34 | 518.2 | Trifluoro Acetate | 76.2 ± 8.3 |
| 218 | 3 | 35 | 551.2 | Trifluoro Acetate | 76.5 ± 1.7 |
| 219 | 5 | 35 | 536.2 | Trifluoro Acetate | 50.4 ± 6.3 |
| 220 | 3 | 36 | 500.3 | Trifluoro Acetate | 56.0 ± 2.9 |
| 221 | 5 | 36 | 484.2 | Trifluoro Acetate | 40.8 ± 8.3 |
| 222 | 4 | 37 | 581.2 | Trifluoro Acetate | 59.0 ± 10.0 |
| 223 | 3 | 38 | 570.2 | Trifluoro Acetate | 63.7 ± 3.1 |
| 224 | 4 | 38 | 571.2 | Trifluoro Acetate | 37.0 ± 0.3 |
| 225 | 3 | 39 | 571.2 | Trifluoro Acetate | 59.5 ± 4.3 |
| 226 | 4 | 39 | 572.2 | Trifluoro Acetate | 37.8 ± 9.2 |
| 227 | 30 | 40 | 535.2 | Trifluoro Acetate | 51.3 ± 10.8 |
| 228 | 31 | 40 | 535.2 | Trifluoro Acetate | 28.9 ± 3.4 |
| 229 | 5 | 41 | 468.2 | Oxalate | 34.7 ± 4.3 |
| 230 | 5 | 42 | 468.2 | Oxalate | 30.8 ± 6.0 |
| 231 | 3 | 43 | 505.2 | Trifluoro Acetate | 65.9 ± 4.2 |
| 232 | 5 | 43 | 490.2 | Trifluoro Acetate | 37.4 ± 2.8 |
| 233 | 3 | 44 | 523.2 | Trifluoro Acetate | 71.0 ± 4.7 |
| 234 | 5 | 44 | 508.2 | Trifluoro Acetate | 44.0 ± 4.4 |
| 235 | 3 | 45 | * | Trifluoro Acetate | 60.5 ± 5.6 |
| 236 | 5 | 45 | 474.2 | Trifluoro Acetate | 36.8 ± 1.6 |
| 237 | 3 | 46 | 507.2 | Trifluoro Acetate | 57.7 ± 1.1 |
| 238 | 5 | 46 | 492.2 | Trifluoro Acetate | 47.6 ± 2.4 |
| 239 | 41 | 4 | 501.2 | Hydrochloride | 49.8 ± 4.5 |
| 240 | 41 | 5 | 519.2 | Hydrochloride | 65.7 ± 3.8 |
| 241 | 41 | 12 | 501.2 | Hydrochloride | 47.0 ± 2.5 |
| 242 | 41 | 29 | 519.2 | Hydrochloride | 55.9 ± 4.0 |
| 243 | 41 | 33 | 500.2 | Hydrochloride | 47.9 ± 3.5 |
| 244 | 41 | 40 | 518.2 | Hydrochloride | 66.6 ± 5.7 |
| 245 | 41 | 34 | 534.2 | Hydrochloride | 56.1 ± 2.9 |
| 246 | 41 | 35 | 552.2 | Hydrochloride | 52.1 ± 2.4 |
| 247 | 41 | 2 | 501.2 | Hydrochloride | 45.4 ± 3.4 |
| 248 | 41 | 3 | 519.2 | Hydrochloride | 47.5 ± 4.8 |
| 249 | 41 | 10 | 553.2 | Hydrochloride | 35.9 ± 2.9 |
| 250 | 41 | 38 | 571.2 | Hydrochloride | 31.6 ± 3.1 |
| 251 | 41 | 39 | 572.2 | Hydrochloride | 33.4 ± 5.7 |
| 252 | 41 | 27 | 536.2 | Hydrochloride | 38.4 ± 3.8 |
| 253 | 41 | 18 | 552.2 | Hydrochloride | 37.6 ± 2.7 |
| 254 | 41 | 16 | 578.2 | Hydrochloride | 50.5 ± 0.8 |
| 255 | 41 | 22 | 510.2 | Hydrochloride | 41.4 ± 3.9 |
| 256 | 41 | 14 | 477.3 | Hydrochloride | 50.6 ± 1.8 |
| 257 | 41 | 13 | 477.2 | Hydrochloride | 49.9 ± 3.4 |
| 258 | 41 | 43 | 506.2 | Hydrochloride | 48.4 ± 5.6 |
| 259 | 41 | 44 | 524.2 | Hydrochloride | 54.1 ± 3.9 |
| 260 | 41 | 45 | 490.2 | Hydrochloride | 38.2 ± 2.0 |
| 261 | 41 | 46 | 508.2 | Hydrochloride | 52.3 ± 6.6 |
| 262 | 43 | 5 | 530.2 | Dihydrochloride | 63.6 ± 4.3 |
| 263 | 17 | 4 | 486.6 | Hydrochloride | 64.3 ± 9.6 |
| 264 | 17 | 2 | 486.6 | Hydrochloride | 39.4 ± 10.1 |
| 265 | 17 | 10 | 535.7 | Hydrochloride | 42.7 ± 9.4 |
| 266 | 17 | 31 | 501.6 | Hydrochloride | 36.7 ± 6.8 |
| 267 | 17 | 36 | 486.6 | Hydrochloride | 37.1 ± 2.5 |
| 268 | 17 | 12 | 483.6 | Hydrochloride | 54.6 ± 8.2 |
| 269 | 17 | 9 | 500.6 | Hydrochloride | 41.3 ± 4.2 |
| 270 | 17 | 40 | 500.6 | Hydrochloride | 56.4 ± 8.3 |
| 271 | 45 | 5 | 526.6 | Hydrochloride | 39.0 ± 0.6 |
| 272 | 45 | 3 | 526.6 | Hydrochloride | 35.7 ± 2.8 |
| 273 | 46 | 5 | 529.6 | Free Base | 40.3 ± 0.5 |
| 274 | 46 | 3 | 529.6 | Free Base | 38.8 ± 1.4 |
| 275 | 47 | 5 | 514.6 | Hydrochloride | 47.0 ± 1.4 |
| 276 | 47 | 3 | 514.6 | Hydrochloride | 53.8 ± 2.0 |
| 277 | 48 | 3 | 536.6 | Hydrochloride | 42.3 ± 11.1 |
| 278 | 48 | 5 | 536.6 | Hydrochloride | 27.5 ± 2.7 |
| 279 | 49 | 3 | 536.6 | Hydrochloride | 17.0 ± 2.7 |
| 280 | 49 | 5 | 536.6 | Hydrochloride | 38.4 ± 5.1 |
| 281 | 50 | 3 | 554.6 | Hydrochloride | 15.6 ± 0.1 |
| 282 | 50 | 5 | 554.6 | Hydrochloride | 17.4 ± 2.1 |
| 283 | 51 | 3 | 554.6 | Hydrochloride | <10 |
| 284 | 51 | 5 | 554.6 | Hydrochloride | 10.8 ± 0.3 |
| 285 | 3 | 2 | 500.2 | Oxalate | 24.6 ± 3.8 |
| 286 | 3 | 33 | 499.1 | Trifluoroacetate | 72.1 ± 4.5 |
| 287 | 5 | 30 | * | Trifluoroacetate | 39.9 ± 4.9 |
| 288 | 5 | 37 | * | Trifluoroacetate | 52.9 ± 7.4 |
| 289 | 5 | 47 | 468.2 | Oxalate | 37.4 ± 7.2 |
| 290 | 5 | 48 | 468.2 | Hydrochloride | 22.7 ± 1.7 |
| 291 | 5 | 49 | 468.2 | Hydrochloride | 18.4 ± n = 1 |
| 292 | 52 | 4 | 503.3 | Trifluoroacetate | 43.5 ± 9.8 |
| 293 | 52 | 5 | 521.3 | Trifluoroacetate | 50.1 ± 5.6 |
| 294 | 52 | 12 | 503.3 | Trifluoroacetate | 43.9 ± 4.4 |
| 295 | 52 | 33 | 502.3 | Trifluoroacetate | 39.7 ± 8.7 |
| 296 | 52 | 40 | 520.2 | Trifluoroacetate | 47.9 ± 4.4 |
| 297 | 21 | 12 | 485.3 | Hydrochloride | 74.5 ± 6.7 |
| 298 | 21 | 31 | 503.4 | Hydrochloride | 54.5 ± 0.8 |
| 299 | 21 | 9 | 502.4 | Hydrochloride | 45.9 ± 3.9 |
| 300 | 21 | 36 | 485.3 | Hydrochloride | 52.2 ± 5.9 |
| 301 | 21 | 40 | 502.4 | Hydrochloride | 69.2 ± 1.2 |
| 302 | 39 | 3 | 536.3 | Hydrochloride | 12.8 ± n = 1 |
| 303 | 40 | 5 | 502.4 | Hydrochloride | 67.9 ± 6.1 |
| 304 | 40 | 10 | 536.3 | Hydrochloride | 44.8 ± 4.9 |
| 305 | 40 | 2 | 484.3 | Hydrochloride | 68.8 ± 6.5 |
| 306 | 40 | 4 | 484.4 | Hydrochloride | 82.4 ± 4.0 |
| 307 | 40 | 12 | 484.3 | Hydrochloride | 74.4 ± 1.8 |
| 308 | 32 | 5 | 503.3 | Hydrochloride | 71.2 ± 5.8 |
| 309 | 54 | 3 | 503.3 | Hydrochloride | 67.1 ± 1.2 |
| 310 | 54 | 5 | 503.3 | Hydrochloride | 72.7 ± 3.4 |
| 311 | 54 | 2 | 485.2 | Trifluoroacetate | 51.5 ± 1.7 |
| 312 | 54 | 4 | 485.4 | Trifluoroacetate | 59.8 ± 3.1 |
| 313 | 53 | 5 | 535.9 | Trifluoroacetate | 29.3 ± 4.1 |
| 314 | 60 | 12 | 518.3 | Trifluoroacetate | 42.0 ± 2.0 |
| 315 | 60 | 29 | 535.9 | Trifluoroacetate | 39.9 ± 2.5 |
| 316 | 60 | 40 | 535.3 | Trifluoroacetate | 58.8 ± 3.1 |
| 317 | 56 | 40 | 535.2 | Trifluoroacetate | 56.4 ± 5.0 |
| 318 | 56 | 33 | 517.2 | Trifluoroacetate | 41.8 ± 3.8 |
| 319 | 56 | 12 | 518.2 | Trifluoroacetate | 49.9 ± 3.9 |
| 320 | 56 | 5 | 536.2 | Trifluoroacetate | 51.4 ± 2.1 |
| 321 | 56 | 4 | 518.2 | Trifluoroacetate | 42.5 ± 2.3 |
| 322 | 57 | 4 | 552.1 | Trifluoroacetate | 27.6 ± 3.9 |
| 323 | 57 | 5 | 570.1 | Trifluoroacetate | 33.8 ± 3.8 |
| 324 | 57 | 12 | 570.2 | Trifluoroacetate | 38.5 ± 6.7 |
| 325 | 57 | 33 | 569.2 | Trifluoroacetate | 31.6 ± 7.8 |
| 326 | 57 | 40 | 569.2 | Trifluoroacetate | 30.4 ± 2.1 |
| 327 | 4 | 46 | 508.2 | Trifluoroacetate | 56.7 ± 2.1 |
| 328 | 4 | 43 | 506.1 | Trifluoroacetate | 57.4 ± 6.5 |
| 329 | 4 | 44 | 524.2 | Trifluoroacetate | 60.2 ± 3.0 |
| 330 | 4 | 45 | 490.2 | Trifluoroacetate | 55.9 ± 2.8 |
| 331 | 58 | 4 | 518.2 | Hydrochloride | 72.9 ± 2.0 |
| 332 | 58 | 5 | 537.2 | Hydrochloride | 80.6 ± 2.4 |
| 333 | 58 | 12 | 518.2 | Hydrochloride | 72.4 ± 3.0 |
| 334 | 58 | 33 | 517.0 | Hydrochloride | 77.8 ± 3.0 |
| 335 | 59 | 4 | 501.2 | Hydrochloride | 66.5 ± 1.8 |
| 336 | 59 | 5 | 519.2 | Hydrochloride | 68.8 ± 2.4 |

TABLE 9-continued

| E.g. | Epoxide | Amine | MSA | Isolated Form | Emax (%) ± SEM |
|---|---|---|---|---|---|
| 337 | 59 | 12 | 501.2 | Hydrochloride | 52.8 ± 3.7 |
| 338 | 59 | 33 | 500.2 | Hydrochloride | 65.5 ± 3.9 |
| 339 | 63 | 5 | 502.3 | Hydrochloride | 40.5 ± 1.2 |
| 340 | 43 | 3 | 530.3 | Di-Hydrochloride | 28.1 ± 2.3 |
| 341 | 63 | 3 | 502.3 | Free Base | 46.2 ± 6.3 |
| 342 | 3 | 34 | 533.2 | Hydrochloride | Not Tested |
| 343 | 5 | 34 | 518.2 | Hydrochloride | Not Tested |
| 344 | 27 | 5 | 519.2 | Hydrochloride | Not Tested |
| 345 | 64 | 5 | 576.1 | Oxalate | 72.1 ± 4.2 |
| 346 | 64 | 29 | 576.1 | Oxalate | 57.3 ± 6.3 |
| 347 | 65 | 5 | 543.3 | Hydrochloride | 84.8 ± 3.4 |
| 348 | 66 | 5 | 532.3 | Trifluoro Acetate | 72.6 ± 5.5 |
| 349 | 67 | 5 | 543.3 | Trifluoro Acetate | 57.4 ± 3.3 |
| 350 | 68 | 5 | 532.3 | Trifluoro Acetate | 45.8 ± 1.9 |
| 351 | 69 | 5 | 543.3 | Trifluoro Acetate | 64.3 ± 1.3 |
| 352 | 70 | 5 | 532.0 | Trifluoro Acetate | 68.5 ± 2.5 |
| 353 | 73 | 5 | 597.3 | Hydrochloride | 96.5 ± 9.7 |
| 354 | 74 | 5 | 502.4 | Hydrochloride | 73.5 ± 2.5 |
| 355 | 32 | 31 | 503.3 | Trifluoroacetate | 66.6 ± 3.3 |
| 356 | 54 | 9 | 502.4 | Trifluoroacetate | 65.2 ± 1.9 |
| 357 | 54 | 31 | 503.2 | Trifluoroacetate | 65.4 ± 2.6 |
| 358 | 54 | 40 | 502.1 | Trifluoroacetate | 68.4 ± 1.5 |
| 359 | 72 | 3 | 517.6 | Trifluoroacetate | 31.2 ± 4.4 |
| 360 | 72 | 5 | 517.3 | Trifluoroacetate | 49.9 ± 3.5 |
| 361 | 32 | 9 | 502.4 | Trifluoroacetate | 70.1 ± 2.2 |
| 362 | 54 | 12 | 485.3 | Trifluoroacetate | 56.2 ± 2.9 |
| 363 | 54 | 36 | 485.3 | Trifluoroacetate | 50.1 ± 4.9 |
| 364 | 32 | 36 | 485.0 | Trifluoroacetate | 69.2 ± 2.5 |
| 365 | 32 | 40 | 502.0 | Trifluoroacetate | 80.2 ± 5.6 |
| 366 | 71 | 3 | 517.2 | Trifluoroacetate | 47.9 ± 3.5 |
| 367 | 71 | 5 | 517.2 | Trifluoroacetate | 69.5 ± 4.6 |
| 368 | 71 | 2 | 499.3 | Trifluoroacetate | 48.4 ± 2.5 |
| 369 | 71 | 4 | 499.4 | Trifluoroacetate | 59.3 ± 3.1 |

* Preparation of product not confirmed by MSA

Representative Procedure 4: Suzuki Coupling
Procedure 4(a)

A compound of formula V (6.4 mmol) is dissolved in 50 ml of dry dioxane and thoroughly flushed with argon. Palladium(0) tetrakis(triphenylphosphine) (750 mg, 0.64 mmol) is added under argon and stirred at ambient temperature until the mixture becomes homogenous. The clear solution is divided into aliquots of 2 ml, and each testing tube is charged with 2 equivalents of an aryl boronic acid of formula IV and 500 μl of 2M aqueous sodium carbonate under argon. The testing tubes are sealed and heated in a microwave oven (MLS ETHOS 1600) for 35 minutes and 100° C. at 1000 W. After complete conversion the samples are diluted with 2 ml of water and extracted with 3 ml of dichloromethane. Extraction is repeated with 2 ml of dichloromethane. The organic solutions are collected and dried over sodium sulfate. The organic filtrate is treated with pre-treated Amberlyst 15 (3 to 4 g each). (Prior to use Amberlyst 15 is prewashed with dichloromethane, ethanol then dichloromethane until the filtrate is colorless). The suspensions are shaken for 30 minutes on an orbital shaker and filtered. The Amberlyst is repeatedly rinsed with dichloromethane/ethanol 1:1 (4×3 ml) and then repeatedly treated with dichloromethane/ethanolic ammonia 1:1. Finally the resin is treated with ethanolic ammonia overnight. The alkaline filtrates are collected and evaporated.

Procedure 4(b)

A mixture of an aryl halide of formula V (1.2 mmol), a boronic acid of formula IV (2.4 mmol), palladium(0) tetrakis (triphenylphosphine) (0.06 mmol), and 2M aqueous sodium carbonate (1.5 ml) in dioxane (20 ml) is heated over night at 100° C. in a sealed tube. The mixture is poured into water and extracted two times with ethyl acetate. The combined organic layers are washed with brine, dried over sodium sulfate, and concentrated under reduced pressure.

The final products prepared via Suzuki coupling may be purified by normal phase chromatography (silica gel, dichloromethane/ethanolic ammonia) providing the free bases or by reverse phase chromatography (acetonitrile/ 0.1% triflouroacetic acid or 0.01% HCl in water) providing the triflouro acetate or hydrochloride salts. The final products existing as salts may also be prepared in a seperate salification step by dissolution of the free base in ethanol or dichloromethane and treatment of the solution with acid, e.g., 1N ethanolic HCl. Removal of all volatiles reduced pressure, affords the desired salt.

The table below sets out representative combinations of aryl halides and boronic acids that are reacted as described above. Preparation of desired product is confirmed via mass spectral analysis (MSA). Emax±Standard Error Mean (SEM) data, discussed in the "Demonstration of Function" section below, is also included for said compounds where available. The Emax values represent the average of at least 3 runs except as otherwise indicated.

TABLE 10

| E.g. | Aryl Halide | Boronic Acid | MSA | Salt Form | Emax (%) ± SEM |
|---|---|---|---|---|---|
| 370 | 2 | 1 | 552.3 | Free Base | 40.3 ± 2.8 |
| 371 | 3 | 1 | 534.2 | Free Base | 38.9 ± 3.9 |
| 372 | 4 | 1 | 552.3 | Free Base | 56.3 ± 4.8 |
| 373 | 1 | 2 | 495.7 | Free Base | 29.0 ± 6.8 |
| 374 | 2 | 2 | 513.5 | Free Base | 49.3 ± 0.3 |
| 375 | 3 | 2 | 495.8 | Free Base | 35.1 ± 7.3 |
| 376 | 4 | 2 | 513.5 | Free Base | 48.2 ± 6.7 |
| 377 | 5 | 2 | 547.2 | Di-Hydrochloride | 33.0 ± 4.2 |
| 378 | 1 | 3 | 500.5 | Free Base | 60.2 ± 3.2 |
| 379 | 2 | 3 | 518.5 | Free Base | 37.7 ± 1.6 |
| 380 | 3 | 3 | 500.3 | Free Base | 57.4 ± 4.1 |
| 381 | 4 | 3 | 518.3 | Trifluoro Acetate | 58.5 ± 6.9 |
| 382 | 5 | 3 | 552.3 | Hydrochloride | 32.3 ± 1.9 |
| 383 | 5 | 10 | 552.1 | Hydrochloride | 52.1 ± 5.4 |
| 384 | 1 | 4 | 550.6 | Free Base | 45.4 ± 5.6 |
| 385 | 2 | 4 | 568.3 | Free Base | 43.1 ± 4.3 |
| 386 | 3 | 4 | 550.7 | Free Base | 46.9 ± 6.7 |
| 387 | 4 | 4 | 568.2 | Trifluoro Acetate | 78.7 ± 14.9 |
| 388 | 1 | 5 | 495.8 | Free Base | <10 |
| 389 | 2 | 5 | 513.5 | Free Base | 20.3 ± 2.0 |
| 390 | 3 | 5 | 495.8 | Free Base | 14.4 ± 1.7 |
| 391 | 4 | 5 | 513.5 | Free Base | 22.5 ± 1.5 |
| 392 | 5 | 5 | 547.4 | Di-Hydrochloride | 17.6 ± 0.4 |
| 393 | 5 | 6 | 586.0 | Hydrochloride | 50.0 ± 3.6 |
| 394 | 5 | 7 | 594.3 | Hydrochloride | 76.9 ± 5.0 |
| 395 | 5 | 8 | 536.3 | Hydrochloride | 46.6 ± 5.9 |
| 396 | 5 | 9 | 566.1 | Hydrochloride | 50.5 ± 1.9 |
| 397 | 6 | 10 | 518.4 | Hydrochloride | 29.9 ± 4.4 |
| 398 | 6 | 3 | 518.4 | Hydrochloride | 22.1 ± 1.7 |
| 399 | 7 | 10 | 536.3 | Hydrochloride | 37.3 ± 3.7 |
| 400 | 7 | 3 | 536.3 | Hydrochloride | 26.0 ± 3.5 |
| 401 | 8 | 10 | 518.4 | Hydrochloride | 46.3 ± 6.8 |
| 402 | 8 | 3 | 518.4 | Trifluoroacetate | 31.1 ± 3.3 |
| 403 | 9 | 10 | 536.3 | Hydrochloride | 57.9 ± 11.2 |
| 404 | 9 | 3 | 536.3 | Hydrochloride | 40.4 ± 7.8 |
| 405 | 1 | 9 | 514.3 | Hydrochloride | 64.4 ± 7.1 |
| 406 | 1 | 6 | 534.0 | Trifluoroacetate | 55.8 ± 7.1 |
| 407 | 1 | 7 | 542.2 | Hydrochloride | 79.7 ± 7.6 |
| 408 | 1 | 8 | 484.3 | Hydrochloride | 74.0 ± 6.5 |
| 409 | 2 | 9 | 532.2 | Hydrochloride | 71.3 ± 3.9 |
| 410 | 2 | 6 | 552.3 | Hydrochloride | 76.0 ± 5.0 |
| 411 | 2 | 7 | 560.3 | Trifluoroacetate | 78.2 ± 9.9 |
| 412 | 2 | 8 | 502.4 | Hydrochloride | 74.4 ± 7.0 |
| 413 | 3 | 9 | 514.3 | Hydrochloride | 66.9 ± 9.2 |
| 414 | 3 | 6 | 534.3 | Trifluoroacetate | 65.7 ± 11.4 |
| 415 | 3 | 7 | 542.3 | Trifluoroacetate | 80.6 ± 5.7 |
| 416 | 3 | 8 | 484.3 | Hydrochloride | 68.9 ± 6.7 |
| 417 | 4 | 9 | 532.2 | Hydrochloride | 79.3 ± 2.4 |
| 418 | 4 | 6 | 552.4 | Hydrochloride | 74.4 ± 6.5 |
| 419 | 4 | 7 | 560.2 | Trifluoroacetate | 87.5 ± 1.8 |
| 420 | 4 | 8 | 502.4 | Hydrochloride | 78.9 ± 2.3 |
| 421 | 10 | 3 | 517.3 | Hydrochloride | 53.4 ± 6.9 |

TABLE 10-continued

| E.g. | Aryl Halide | Boronic Acid | MSA | Salt Form | Emax (%) ± SEM |
|---|---|---|---|---|---|
| 422 | 10 | 9 | 531.3 | Hydrochloride | 60.1 ± 8.2 |
| 423 | 10 | 6 | 551.4 | Hydrochloride | 63.1 ± 4.7 |
| 424 | 10 | 7 | 559.1 | Hydrochloride | 71.2 ± 7.9 |
| 425 | 10 | 8 | 501.3 | Hydrochloride | 67.1 ± 3.0 |
| 426 | 11 | 3 | 517.3 | Hydrochloride | 61.0 ± 7.1 |
| 427 | 11 | 9 | 531.3 | Hydrochloride | 72.4 ± 6.9 |
| 428 | 11 | 6 | 551.3 | Hydrochloride | 75.5 ± 6.9 |
| 429 | 11 | 7 | 559.3 | Trifluoroacetate | 84.7 ± 12.3 |
| 430 | 11 | 8 | 501.3 | Hydrochloride | 77.4 ± 9.0 |
| 431 | 12 | 3 | 500.3 | Hydrochloride | 50.3 ± 7.8 |
| 432 | 12 | 9 | 514.3 | Hydrochloride | 60.7 ± 8.4 |
| 433 | 12 | 6 | 534.2 | Hydrochloride | 56.5 ± 11.0 |
| 434 | 12 | 7 | 542.3 | Trifluoroacetate | 73.1 ± 5.1 |
| 435 | 12 | 8 | 484.3 | Hydrochloride | 61.4 ± 6.1 |
| 436 | 13 | 3 | 518.4 | Hydrochloride | 57.5 ± 12.0 |
| 437 | 13 | 9 | 532.2 | Hydrochloride | 72.0 ± 10.5 |
| 438 | 13 | 6 | 552.3 | Hydrochloride | 64.3 ± 12.4 |
| 439 | 13 | 7 | 560.1 | Trifluoroacetate | 75.0 ± 9.6 |
| 440 | 13 | 8 | 502.4 | Hydrochloride | 73.4 ± 4.4 |
| 441 | 14 | 3 | 500.3 | Hydrochloride | 64.2 ± 7.0 |
| 442 | 14 | 9 | 514.3 | Hydrochloride | 61.5 ± 3.0 |
| 443 | 14 | 6 | 534.2 | Hydrochloride | 56.1 ± 11.2 |
| 444 | 14 | 7 | 542.3 | Trifluoroacetate | 83.8 ± 11.4 |
| 445 | 14 | 8 | 484.3 | Hydrochloride | 74.5 ± 14.1 |
| 446 | 4 | 3 | 518.5 | Hydrochloride | 64.0 ± 6.0 |

Example 447

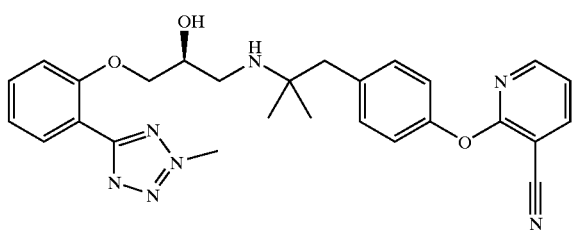

A solution of Amine 4 (300 mg, 1.130 mmol) and trimethylsilyl acetamide (TMSA) (210 mg, 1.614 mmol) is dissolved in acetonitrile (1.5 mL) and stirred for 30 minutes. To this solution is added Epoxide 62 (250 mg, 1.076 mmol) in acetonitrile (3 mL) and ytterbium triflate (13 mg, 0.215 mmol). The solution is heated at 80° C. for 24 hours and concentrated in vacuo. The resulting solid is purified by flash column chromatography (99% dichloromethane:1% methanol gradient to (95% dichloromethane:5% methanol as eluent) to give 135 mg of the title compound (25%). FDMS m/e=500 (M$^+$+1). Emax (±SEM)=74.5 (4.0).

Example 448

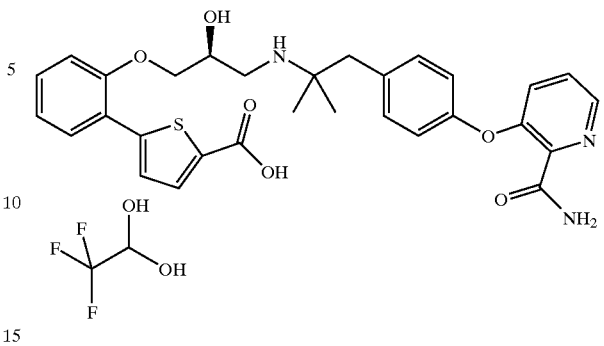

The compound of Example 346 is hydrolized with 1.0 equivalent of lithium hydroxide (1M), in tetrahydrofuran at room temperature overnight, and then concentrated to a crude residue which is purified via HPLC as the trifluoroacetic acid salt as described above in Representative Procedure 2 and 3. MS 562.2. Emax (±SEM)=79.9 (5.5).

Example 449

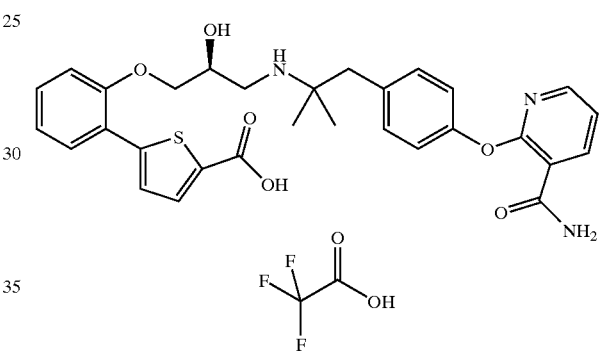

The title compound is prepared from the compound of Example 345 as described in Example 448. MS 562.2. Emax (±SEM)=74.2 (2.2).

Example 450

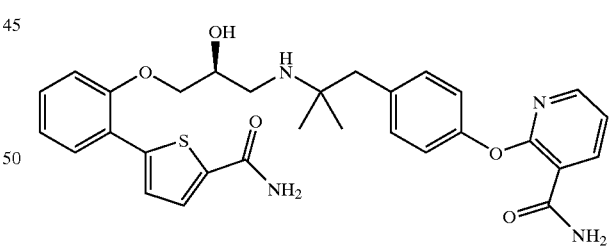

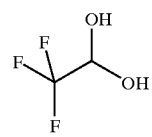

The compound of Example 345 in dimethylformamide is treated with 1.0 equivalent of sodium ethoxide and 4.0 equivalents of formamide. The mixture is heated to 100° C. for 4 hours, cooled to room temperature then concentrated. The residue is purified via HPLC as the trifluoroacetic acid salt as described above in Representative Procedure 2 and 3. MS 561.2. Emax (±SEM)=67.4 (2.1).

Example 451

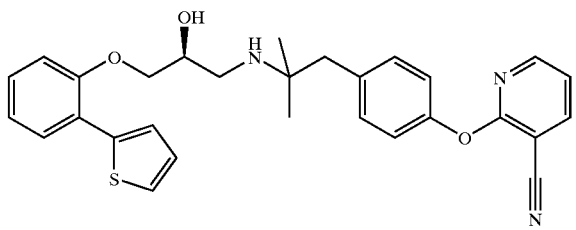

The compound of Example 50 (250 mg) and 0.5 molar equivalents (29 mg) of fumaric acid are suspended in 5 mL of ethanol denatured with toluene and the mixture is heated mildly to effect dissolution. After approximately five minutes, the solution begins to precipitate. The temperature of the crystal slurry is maintained at the crystallization temperature (56–57° C.) for about one hour. The heat source is then turned off and the slurry is allowed to cool with stirring overnight. Ethanol denatured with toluene (2 mL) is added and the solids are isolated by vacuum filtration. The filter cake is washed with ethanol denatured with toluene (5 mL) and air dried to give 230 mg of the title compound. mp=147–149° C. (measured by differential scanning calorimetry (DSC) with a scan rate of 10° C./minute).

Example 452

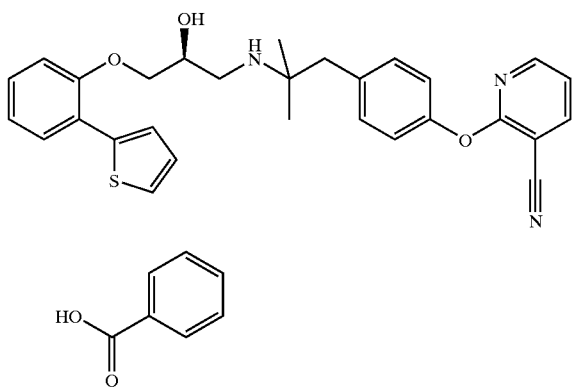

The compound of Example 50 (57.7 mg) is dissolved in 2.5 mL of absolute ethanol and the solution is stirred at room temperature. To the stirred solution is added benzoic acid (1 equivalent, 14.1 mg) dissolved in 200 microliters of methanol. The resulting mixture is stirred at room temperature for 3.5 to 4 hours. Precipitation occurrs in approximately 30–60 minutes. The precipitate is isolated by vacuum filtration and the filter cake is collected and air-dried overnight. mp=148–150° C. (measured by DSC with a scan rate of 5° C./minute).

Example 453

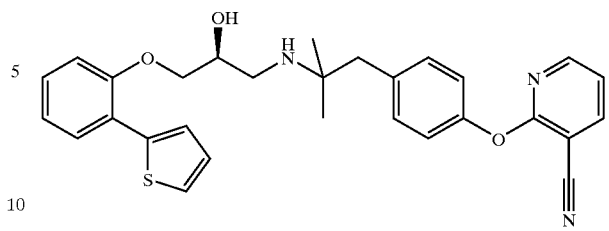

The compound of Example 50 (200 mg) is dissolved in 1 mL of acetone and the solution is stirred at room temperature. To the stirred solution is added R-mandelic acid (1 equivalent, 61 mg) in acetone (1 ml). The resulting mixture is stirred at room temperature and the precipitate is isolated by vacuum filtration. The filter cake is collected and air dried overnight. mp=138–140° C. (measured by DSC with a scan rate of 5° C./minute).

Example 454

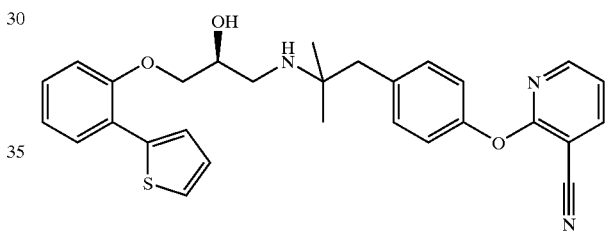

The compound of Example 50 (106 mg) is dissolved in 1 mL of ethyl acetate and the solution is stirred at room temperature. To the stirred solution is added salicylic acid (1 equivalent, 29 mg) in 150 microliters of methanol. The resulting mixture is stirred at room temperature and then heated up to 50° C. Hexane is added to the mixture as an antisolvent at elevated temperature until cloud point (approxiamtely 1 ml ethyl acetate:1 ml of hexane). The slurry is allowed to slowly cool to room temperature. The precipitate is isolated by vacuum filtration and the filter cake is collected and air dried overnight. mp=124° C. (peak max) (measured by DSC with a scan rate of 5° C./minute).

Demonstration of Function

The genes encoding the human $\beta_1$-adrenergic receptor (Frielle et al., *Proc. Natl. Acad. Sci.,* 84:7920–7924, 1987), the human $\beta_2$-adrenergic receptor (Kobika et al., *Proc. Natl. Acad. Sci.,* 84:46–50, 1987, Emorine et al., *Proc. Natl. Acad. Sci.,* 84:6995–6999, 1987) and the human $\beta_3$ adrenergic receptor (Granneman et al., *Molecular Pharmacology,* 44(2) :264–70, 1993) are individually subcloned into a phd expression vector (Grinnell et al., *Bio/Technology,* 5:1189–1192, 1987) and transfected into the DXB-11 Chinese hamster ovary (CHO) cell line by calcium phosphate precipitation methodology. The stably transfected cells are grown to 95% confluency in 95% Dulbecco's modified Eagles Medium (DMEM), 5% fetal bovine serum and 0.01% proline. Media is removed and the cells are washed with phosphate buffered (pH 7.4) saline (without magnesium and calcium). Cells are then lifted using an enzyme free cell dissociation solution (Specialty Media, Lavallette, N.J.) and pelleted by centrifugation.

Cells from each of the above cell lines are resuspended and added (20,000/well) to a 96-well plate. Cells are incubated at 37° C. with representative compounds of the invention for 20 minutes in buffer (Hank's balanced salt solution, 10 mM HEPES, 0.1% BSA, 1 mM L-ascorbic acid, 0.2% dimethyl sulfoxide, 1 mm 3-isobutyl-1-methylxanthine, pH 7.4). After halting the incubation with quench buffer (50 mM Na Acetate, 0.25% Triton X-100, pH 5.8), the c-AMP level is quantified by scintillation proximity assay (SPA) using a modification of the commercially available c-AMP kit (Amersham, Arlington Heights, Ill.) with rabbit anti-cAMP antibody (ICN Biomedicals, Aurora, Ohio) for the kit.

Sigmoidal dose response curves, from the whole cell receptor coupled c-AMP assay are fit to a four parameter logistic equation using non linear regression: $y=(a-d)/(1+(Dose/c)^b)+d$ where a and d are responses at zero and maximal dose, b is the slope factor and c is the $EC_{50}$ as previously described (DeLean et al., *Am. J. Physiol.*, 235, E97–E102, 1978). $EC_{50}$ is assessed as the concentration producing 50% of the maximum response to each agonist.

Isoproterenol is accepted in the art as a non-selective $\beta_3$ agonist and is widely used as a comparator in evaluating the activity of compounds. See *Trends in Pharm. Sci.*, 15:3, 1994. The % intrinsic activity ($E_{max}$) of representative compounds of the invention is assessed relative to isoproterenol by the compound's maximal response divided by the isoproterenol maximal response times 100.

In vitro Rat Atrial Tachycardia

Male rats (250–350 g) (Harlan Sprague Dawley, Indianapolis, Ind., USA) are killed by cervical dislocation. Hearts are removed and the left and right atria are dissected and mounted with thread in tissue baths containing 10 mls of modified Krebs' solution. Initial resting tension is 1.5–2.0 g at the outset of the experiment (*Naunyn-Schmied Arch. Pharmacol.*, 320:145, 1982). Tissues are allowed to equilibrate approximately 30 minutes with vigorous oxygenation before exposure to a compound of the invention.

To evaluate the ability of test compounds to increase heart rate, representative compounds of the present invention are added cumulatively once the atrial rate reached a steady state from the previous addition. Compound addition is continued until no further increase in atrial rate occurred or until a concentration of $10^{-4}M$ is reached. The increase in beats per minute (bpm) is measured for each concentration of test compound by means of a BioPac System (*Br. J. of Pharmacol.*, 126:1018–1024, 1999).

Utilities

As agonists of the $\beta_3$ receptor, a compound of the present invention is useful in treating conditions in human and non-human animals in which the $\beta_3$ receptor has been demonstrated to play a role. The diseases, disorders or conditions for which compounds of the present invention are useful in treating or preventing include, but are not limited to, (1) diabetes mellitus, (2) hyperglycemia, (3) obesity, (4) hyperlipidemia, (5) hypertriglyceridemia, (6) hypercholesterolemia, (7) atherosclerosis of coronary, cerebrovascular and peripheral arteries, (8) gastrointestinal disorders including peptid ulcer, esophagitis, gastritis and duodenitis, (including that induced by *H. pylori*), intestinal ulcerations (including inflammatory bowel disease, ulcerative colitis, Crohn's disease and proctitis) and gastrointestinal ulcerations, (9) neurogenic inflammation of airways, including cough, asthma, (10) depression, (11) prostate diseases such as benign prostate hyperplasia, (12) irritable bowel syndrome and other disorders needing decreased gut motility, (13) diabetic retinopathy, (14) neuropathic bladder dysfunction, (15) elevated intraocular pressure and glaucoma and (16) non-specific diarrhea dumping syndrome.

In treating non-human, non-companion animals, the compounds of the present invention are useful for increasing weight gain and/or improving the feed utilization efficiency and/or increasing lean body mass and/or decreasing birth mortality rate and increasing post/natal survival rate.

Formulation

The compound of formula I is preferably formulated in a unit dosage form prior to administration. Therefore, yet another embodiment of the present invention is a pharmaceutical formulation comprising a compound of formula I and a pharmaceutical carrier.

The present pharmaceutical formulations are prepared by known procedures using well-known and readily available ingredients. In making the formulations of the present invention, the active ingredient (formula I compound) will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

Formulation Examples

Formulation 1

Tablets

| Ingredient | Quantity (mg/tablet) |
|---|---|
| Active Ingredient | 5–500 |
| Cellulose, microcrystalline | 200–650 |
| Silicon dioxide, fumed | 10–650 |
| Stearate acid | 5–15 |

The components are blended and compressed to form tablets.

Formulation 2

Suspensions

| Ingredient | Quantity (mg/5 ml) |
|---|---|
| Active Ingredient | 5–500 mg |
| Sodium carboxymethyl cellulose | 50 mg |
| Syrup | 1.25 mg |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Formulation 3

Intravenous Solution

| Ingredient | Quantity |
|---|---|
| Active Ingredient | 25 mg |
| Isotonic saline | 1,000 ml |

The solution of the above ingredients is intravenously administered to a patient at a rate of about 1 ml per minute.

Dose

The specific dose administered is determined by the particular circumstances surrounding each situation. These circumstances include, the route of administration, the prior medical history of the recipient, the pathological condition or symptom being treated, the severity of the condition/symptom being treated, and the age and sex of the recipient. However, it will be understood that the therapeutic dosage administered will be determined by the physician in the light of the relevant circumstances.

Generally, an effective minimum daily dose of a compound of formula I is about 5, 10, 15, or 20 mg. Typically, an effective maximum dose is about 500, 100, 60, 50, or 40 mg. Most typically, the dose ranges between 15 mg and 60 mg. The exact dose may be determined, in accordance with the standard practice in the medical arts of "dose titrating" the recipient; that is, initially administering a low dose of the compound, and gradually increasing the does until the desired therapeutic effect is observed.

Route of Administration

The compounds can be administered by a variety of routes including the oral, rectal, transdermal, subcutaneous, topical, intravenous, intramuscular or intranasal routes.

Combination Therapy

A compound of formula I may be used in combination with other drugs that are used in the treatment/prevention/suppression or amelioration of the diseases or conditions for which compounds of formula I are useful. Such other drug(s) may be administered, by a route and in an amount commonly used therefor, contemporaneously or sequentially with a compound of formula I. When a compound of formula I is used contemporaneously with one or more other drugs, a pharmaceutical unit dosage form containing such other drugs in addition to the compound of formula I is preferred. Accordingly, the pharmaceutical compositions of the present invention include those that also contain one or more other active ingredients, in addition to a compound of formula I. Examples of other active ingredients that may be combined with a compound of formula I, either administered separately or in the same pharmaceutical compositions, include, but are not limited to:

(a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(b) insulin or insulin mimetics;

(c) sulfonylureas such as tolbutamide and glipizide;

(d) alpha-glucosidase inhibitors (such as acarbose);

(e) cholesterol lowering agents such as
  i. HMG-CoA reductase inhibitors (lovastatin, simvastatin and pravastatin, fluvastatin, atorvastatin, and other statins),
  ii. sequestrants (cholestyramine, colestipol and a dialkylaminoalkyl derivatives of a cross-linked dextran),
  iii. nicotinyl alcohol nicotinic acid or a salt thereof,
  iv. proliferator-activator receptor a agonists such as fenofibric acid derivatives (gemfibrozil, clofibrat, fenofibrate and benzafibrate),
  v. inhibitors of cholesterol absorption for example beta-sitosterol and (acyl CoA:cholesterol acyltransferase) inhibitors for example melinamide,
  vi. probucol,
  vii. vitamin E, and
  viii. thyromimetics;

(f) PPARδ agonists such as those disclosed in WO97/28149;

(g) antiobesity compounds such as fenfluramine, dexfenfluramine, phentermine, sibutramine, orlistat, and other $\beta_3$ adrenergic receptor agonists;

(h) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;

(i) PPARα agonists as described in WO 97/36579 by Glaxo;

(j) PPARγ antagonists as described in WO97/10813; and (k) serotonin reuptake inhibitors such as fluoxetine and sertraline.

We claim:

1. A compound of formula I:

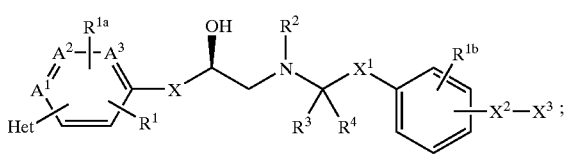

(I)

wherein:
  $A^1$, $A^2$ and $A^3$ are carbon or nitrogen provided that only one of $A^1$, $A^2$ and $A^3$ can be nitrogen;
  Het is an optionally substituted, optionally benzofused 5 or 6 membered heterocyclic ring;
  $R^1$, $R^{1a}$ and $R^{1b}$ are independently H, halo, hydroxy, $C_1$–$C_6$ alkyl, $C_1$–$C_6$ alkoxy, $C_1$–$C_4$ haloalkyl, or $SO_2$ ($C_1$–$C_6$ alkyl);

$R^2$ is H or $C_1$–$C_6$ alkyl;

$R^3$ is H or $C_1$–$C_6$ alkyl;

$R^4$ is H or $C_1$–$C_6$ alkyl;

or $R^3$ and $R^4$ combine with the carbon to which both are attached to form a $C_3$–$C_6$ cyclic ring;

or $R^4$ and $X^1$ combine with the carbon to which both are attached to form a $C_3$–$C_8$ cyclic ring;

or $R^4$ combines with $X^1$, the carbon to which both are attached, and the phenyl group to which $X^1$ is attached to form:

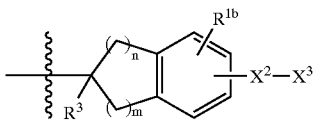

wherein:
n and m are independently 0, 1, 2, or 3 provided that the sum of n+m is ≦4 and that $R^3$ is H;

X is $OCH_2$, $SCH_2$ or a bond;

$X^1$ is a bond or a $C_1$–$C_5$ divalent hydrocarbon moiety;

$X^2$ is O, S, NH, $NHSO_2$, $SO_2NH$, $CH_2$ or a bond; and $X^3$ is optionally substituted phenyl or an optionally substituted 5 or 6 membered heterocyclic ring; or a pharmaceutical salt thereof.

2. The compound of claim 1 wherein:

$A^1$, $A^2$ and $A^3$ are carbon;

Het is optionally substituted one to three times independently with halo, hydroxy, oxo, cyano, nitro, phenyl, benzyl, $C_1$–$C_4$ alkyl, $C_1$–$C_4$ haloalkyl, $C_1$–$C_4$ alkoxy, $COR^8$, $CO_2R^8$, $CONR^8R^8$, $NR^8R^8$, $NHCO(C_1$–$C_4$ alkyl), NHCO(phenyl), NHCO(benzyl), $SR^8$, $SO(C_1$–$C_4$ alkyl), $SO_2(C_1$–$C_4$ alkyl), $SO_2(NR^8R^8)$, $OCO(C_1$–$C_4$ alkyl), $OCO_2R^8$ or $OCONR^8R^8$;

$R^1$, $R^{1a}$ and $R^{1b}$ are independently H, halo, $C_1$–$C_4$ alkyl, $C_1$–$C_4$ alkoxy, $C_1$–$C_4$ haloalkyl, or $SO_2(C_1$–$C_4$ alkyl);

$R^2$ is H or $C_1$–$C_4$ alkyl;

$R^3$ and $R^4$ are independently H or $C_1$–$C_4$ alkyl;

or $R^3$ and $R^4$ combine with the carbon to which both are attached to form a $C_3$–$C_6$ cyclic ring;

or $R^4$ and $X^1$ combine with the carbon to which both are attached to form a $C_3$–$C_8$ cyclic ring;

or $R^4$ combines with $X^1$, the carbon to which both are attached, and the phenyl group to which $X^1$ is attached to form:

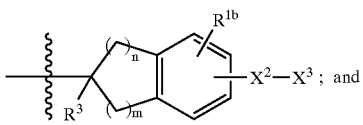

$X^3$ is optionally substituted one to three times independently with halo, hydroxy, oxo, cyano, nitro, phenyl, benzyl, $C_1$–$C_4$ alkyl, $C_1$–$C_4$ haloalkyl, $C_1$–$C_4$ alkoxy, $COR^8$, $CO_2R^8$, $CONR^8R^8$, $NR^8R^8$, $NHCO(C_1$–$C_4$ alkyl), NHCO(phenyl), NHCO(benzyl), $SR^8$, $SO(C_1$–$C_4$ alkyl), $SO_2(C_1$–$C_4$ alkyl), $SO_2(NR^8R^8)$, $OCO(C_1$–$C_4$ alkyl), $OCO_2R^8$ or $OCONR^8R^8$; and $R^8$ is independently at each occurrence H or $C_1$–$C_4$ alkyl;

or a pharmaceutical salt thereof.

3. The compound of claim 2 of the formula:

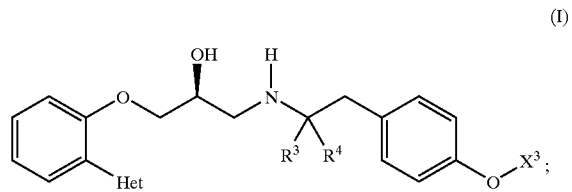

(I)

wherein:

Het is selected from furan; isothiazole; isoxazole; oxazole; and thiophene; wherein said Het moieties are optionally substituted once with fluorine, methyl, cyano, $SO_2NH_2$ or $COCH_3$;

$R^3$ and $R^4$ are independently H or methyl;

$X^3$ is phenyl, pyridyl or pyridazinyl wherein said $X^3$ moieties are substituted once or twice with chloro, cyano, $CONH_2$ or $SO_2CH_3$; or a pharmaceutical salt thereof.

4. The compound of claim 3 wherein Het is thien-2-yl optionally substituted once with fluorine, methyl, cyano, $SO_2NH_2$ or $COCH_3$; $R^3$ and $R^4$ are both methyl; and $X^3$ is phenyl or pyridyl wherein said $X^3$ moieties are substituted once with cyano or $CONH_2$; or a pharmaceutical salt thereof.

5. The compound of claim 4 wherein $X^3$ is pyridyl substituted once with cyano or $CONH_2$; or a pharmaceutical salt thereof.

6. The compound of claim 5 which is selected from the group consisting of:

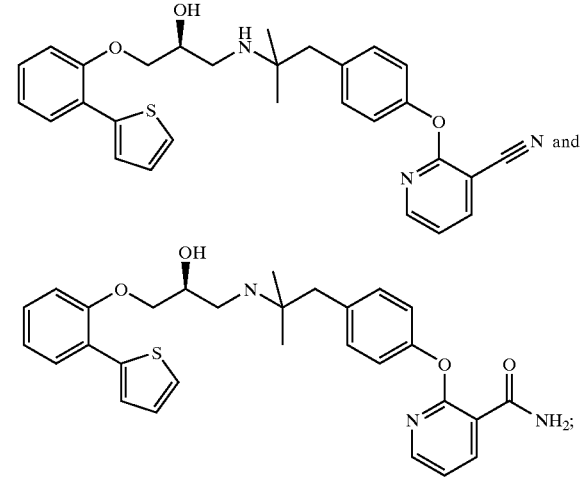

or a pharmaceutical salt thereof.

7. A compound of the formula:

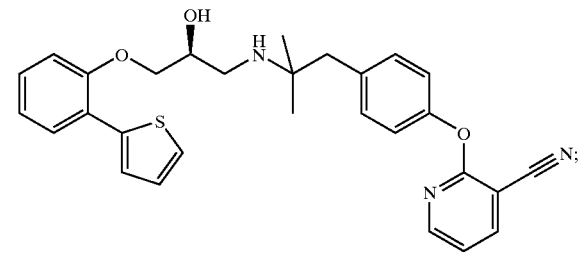

or a pharmaceutical salt thereof.

8. The compound of claim 7 which is the hydrochloride salt.

9. The compound of claim 7 which is the hemi-fumarate, benzoate, salicylate or R-mandelate salt.

10. A method of treating obesity comprising administering to a patient in need thereof a compound of claim 3.

11. A method of treating Type II Diabetes comprising administering to a patient in need thereof a compound of claim 3.

12. A compound of formula II:

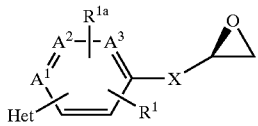

wherein:

$A^1$, $A^2$ and $A^3$ are carbon or nitrogen provided that only one of $A^1$, $A^2$ and $A^3$ can be nitrogen;

Het is an optionally substituted, optionally benzofused 5 or 6 membered heterocyclic ring;

$R^1$ and $R^{1a}$ are independently H, halo, hydroxy, $C_1$–$C_6$ alkyl, $C_1$–$C_6$ alkoxy, $C_1$–$C_4$ haloalkyl, or $SO_2(C_1$–$C_6$ alkyl); or a salt thereof.

13. The compound of claim 12 of the formula:

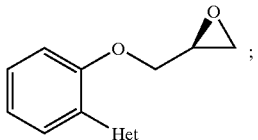

wherein:

Het is selected from benzothiophene; furan; isothiazole; isoxazole; oxazole; thiophene; and thiazole; wherein said Het moieties are optionally substituted once with fluorine, chlorine, methyl, cyano, $SO_2NH_2$ or $COCH_3$; or a salt thereof.

14. A process for preparing a compound of claim 1 which comprises reacting a compound of formula II:

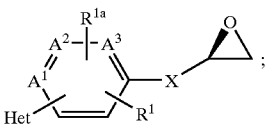

with a compound of formula III:

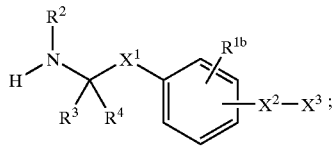

in the presence of a suitable solvent.

15. A method of treating obesity comprising administering to a patient in need thereof a compound of claim 7.

16. A method of treating obesity comprising administering to a patient in need thereof a compound of claim 8.

17. A method of treating obesity comprising administering to a patient in need thereof a compound of claim 9.

* * * * *

UNITED STATES PATENT AND TRADEMARK OFFICE
CERTIFICATE OF CORRECTION

PATENT NO. : 6,730,792 B2
APPLICATION NO. : 10/311112
DATED : May 4, 2004
INVENTOR(S) : Evers et al.

Page 1 of 1

It is certified that error appears in the above-identified patent and that said Letters Patent is hereby corrected as shown below:

On Title Page (75): Inventors: after "David Michael Remick, Fishers, IN (US);" and prior to "Daniel Jon Sall, Greenwood, IN (US);" please insert --Gerd Ruehter, Hamburg (DE)--;

And after "Daniel Jon Sall, Greenwood, IN (US);" and prior to "Miles Goodman Siegal. Indianapolis, IN (US);" please insert --Theo Schotten, Vierhoefen (DE)--.

Signed and Sealed this

Nineteenth Day of September, 2006

JON W. DUDAS
*Director of the United States Patent and Trademark Office*